United States Patent
Bettoun

(10) Patent No.: US 11,988,675 B2
(45) Date of Patent: May 21, 2024

(54) METHODS FOR QUANTIFYING FRATAXIN ACTIVITY

(71) Applicant: Larimar Therapeutics, Inc., Bala Cynwyd, PA (US)

(72) Inventor: Joan David Bettoun, Elkins Park, PA (US)

(73) Assignee: Larimar Therapeutics, Inc., Bala Cynwyd, PA (US)

( * ) Notice: Subject to any disclaimer, the term of this patent is extended or adjusted under 35 U.S.C. 154(b) by 371 days.

(21) Appl. No.: 17/105,149

(22) Filed: Nov. 25, 2020

(65) Prior Publication Data

US 2021/0156874 A1    May 27, 2021

Related U.S. Application Data

(60) Provisional application No. 62/940,214, filed on Nov. 25, 2019.

(51) Int. Cl.
*G01N 33/68* (2006.01)
*G01N 33/53* (2006.01)

(52) U.S. Cl.
CPC ..... *G01N 33/6893* (2013.01); *G01N 33/5306* (2013.01); *G01N 2333/902* (2013.01)

(58) Field of Classification Search
None
See application file for complete search history.

(56) References Cited

U.S. PATENT DOCUMENTS

| | | |
|---|---|---|
| 11,459,363 B2 | 10/2022 | Payne |
| 2014/0135275 A1 | 5/2014 | Keefe et al. |
| 2014/0308262 A1 | 10/2014 | Lorberboum-Galski |
| 2016/0060605 A1 | 3/2016 | Testi |
| 2017/0327847 A1 | 11/2017 | Ghadessy et al. |
| 2018/0333386 A1 | 11/2018 | Cortopassi et al. |
| 2019/0076429 A1 | 3/2019 | Rufini et al. |
| 2020/0377951 A1 | 12/2020 | Bettoun |
| 2021/0355177 A1 | 11/2021 | Bettoun et al. |
| 2021/0363205 A1 | 11/2021 | Bettoun |
| 2022/0193190 A1 | 6/2022 | Boyle et al. |
| 2022/0276258 A1 | 9/2022 | Bettoun et al. |

(Continued)

FOREIGN PATENT DOCUMENTS

| | | |
|---|---|---|
| CA | 2649538 A1 | 11/2007 |
| EP | 1752536 A1 | 2/2007 |

(Continued)

OTHER PUBLICATIONS

Correia et al., "Conformational stability of human frataxin and effect of Friedreich's ataxia-related mutations on protein folding" Biochemical Journal, vol. 398(3), pp. 605-611. (Year: 2006).*

(Continued)

*Primary Examiner* — Michelle F. Paguio Frising
*Assistant Examiner* — Grant C Currens
(74) *Attorney, Agent, or Firm* — McCarter & English, LLP; Jill Mello; Yelena Margolin

(57) ABSTRACT

The present disclosure provides methods, compositions and kits for measuring activity of a frataxin (FXN) protein, e.g., an FXN fusion protein. The present invention also provides methods for identifying compounds capable of modulating activity of an FXN protein, e.g., an FXN fusion protein.

25 Claims, 15 Drawing Sheets

Specification includes a Sequence Listing.

(56) References Cited

U.S. PATENT DOCUMENTS

| | | |
|---|---|---|
| 2022/0378869 A1 | 12/2022 | Bettoun |
| 2023/0242600 A1 | 8/2023 | Payne |

FOREIGN PATENT DOCUMENTS

| | | |
|---|---|---|
| EP | 2750686 A1 | 7/2014 |
| WO | 2005/116204 A1 | 12/2005 |
| WO | 2006/108581 A2 | 10/2006 |
| WO | 2007/124082 A2 | 11/2007 |
| WO | 2011/103536 A1 | 8/2011 |
| WO | 2012/014083 A2 | 2/2012 |
| WO | 2012/174452 A1 | 12/2012 |
| WO | 2013/036596 A2 | 3/2013 |
| WO | 2013/071440 A1 | 5/2013 |
| WO | 2016/119856 A1 | 8/2016 |
| WO | 2016/172659 A1 | 10/2016 |
| WO | 2017/161354 A1 | 9/2017 |
| WO | 2017/165167 A1 | 9/2017 |
| WO | 2021/011929 A1 | 1/2021 |
| WO | 2021/021931 A1 | 2/2021 |
| WO | 2021/195597 A2 | 9/2021 |

OTHER PUBLICATIONS

Bencze et al., "The Structure and Function of Frataxin", Critical Reviews in Biochemistry and Molecular Biology, vol. 41(5), pp. 269-291. (Year: 2006).*

Bou-Abdallah et al., "Iron Binding and Oxidation Kinetics in Frataxin CyaY of *Escherichia coli*", Journal of Molecular Biology, vol. 341, pp. 605-615. (Year: 2004).*

Raynal et al., "Quality assessment and optimization of purified protein samples: why and how?", Microbial Cell Factories, vol. 13(180), pp. 1-10. (Year: 2014).*

Khdour et al., Lipophilic methylene blue analogues enhance mitochondrial function and increase frataxin levels in a cellular model of Friedreich's ataxia. Bioorg Med Chem. Jul. 23, 2018;26(12):3359-3369.

Pandolfo, Drug Insight: antioxidant therapy in inherited ataxias. Nat Clin Pract Neurol. Feb. 2008;4(2):86-96.

Shoichet et al., Frataxin promotes antioxidant defense in a thiol-dependent manner resulting in diminished malignant transformation in vitro. Hum Mol Genet. Apr. 1, 2002;11(7):815-21.

Vyas et al., A TAT-frataxin fusion protein increases lifespan and cardiac function in a conditional Friedreich's ataxia mouse model. Hum Mol Genet. Mar. 15, 2012;21(6):1230-47.

International Search Report and Written Opinion for Application No. PCT/US2020/062355, dated Mar. 12, 2021, 13 pages.

Abrahao et al., Milestones in Friedreich ataxia: more than a century and still learning. Neurogenetics. Jul. 2015;16(3):151-60.

Belbellaa et al., High Levels of Frataxin Overexpression Lead to Mitochondrial and Cardiac Toxicity in Mouse Models. Mol Ther Methods Clin Dev. Sep. 1, 2020;19:120-138.

European Medicines Agency, Public summary of opinion on orphan designation: Human Frataxin fused to TAT cell-penetrating peptide for the treatment of Friedreich's ataxia. Nov. 13, 2020. One page.

Guo et al., Liquid Chromatography-High Resolution Mass Spectrometry Analysis of Platelet Frataxin as a Protein Biomarker for the Rare Disease Friedreich's Ataxia. Anal Chem. Feb. 6, 2018;90(3):2216-2223.

Han et al., Mechanisms of iron and copper-frataxin interactions. Metallomics. Aug. 16, 2017;9(8):1073-85.

Hayashi et al., Oxidative stress in inherited mitochondrial diseases. Free Radic Biol Med. Nov. 2015;88(Pt A):10-7.

Lu et al., Frataxin deficiency induces Schwann cell inflammation and death. Biochim Biophys Acta. Nov. 2009;1792(11):1052-61.

Mastrangelo, Clinical approach to neurodegenerative disorders in childhood: an updated overview. Acta Neurol Belg. Dec. 2019;119(4):511-21.

Mathis et al., The ataxic neuropathies. J Neurol. Oct. 2021;268(10):3675-3689.

Sasarman et al., Tissue-specific responses to the LRPPRC founder mutation in French Canadian Leigh Syndrome. Hum Mol Genet. Jan. 15, 2015;24(2):480-91.

Schultz et al., Off-target effects dominate a large-scale RNAi screen for modulators of the TGF-β pathway and reveal microRNA regulation of TGFBR2. Silence. Mar. 14, 2011;2:3, 20 pages.

International Search Report and Written Opinion for Application No. PCT/US2020/044069, dated Oct. 28, 2020, 12 pages.

International Search Report and Written Opinion for Application No. PCT/US2020/044400, dated Oct. 22, 2020, 19 pages.

International Search Report and Written Opinion for Application No. PCT/US2021/030348, dated Aug. 9, 2021, 24 pages.

International Search Report and Written Opinion for Application No. PCT/US2021/063163, dated Apr. 11, 2022, 16 pages.

Internatonal Search Report and Written Opinion for Application No. PCT/US2020/042683, dated Nov. 4, 2020, 12 pages.

U.S. Appl. No. 16/942,276, filed Jul. 29, 2020, U.S. Pat. No. 11,459,363, Issued.

U.S. Appl. No. 17/900,450, filed Aug. 31, 2022, 2023-0242600, Published.

U.S. Appl. No. 17/627,638, filed Jan. 14, 2022, 2022-0378869, Published.

U.S. Appl. No. 17/631,414, filed Jan. 28, 2022, 2022-0276258, Published.

U.S. Appl. No. 17/246,549, filed Apr. 30, 2021, 2021-0363205, Allowed.

U.S. Appl. No. 18/433,336, filed Feb. 5, 2024, Pending.

U.S. Appl. No. 17/549,770, filed Dec. 13, 2021, 2022-0193190, Published.

* cited by examiner

```
                          SEQUENCE LISTING

<160> NUMBER OF SEQ ID NOS: 12

<210> SEQ ID NO 1
<211> LENGTH: 210
<212> TYPE: PRT
<213> ORGANISM: Homo sapiens

<400> SEQUENCE: 1

Met Trp Thr Leu Gly Arg Arg Ala Val Ala Gly Leu Leu Ala Ser Pro
1               5                   10                  15

Ser Pro Ala Gln Ala Gln Thr Leu Thr Arg Val Pro Arg Pro Ala Glu
            20                  25                  30

Leu Ala Pro Leu Cys Gly Arg Arg Gly Leu Arg Thr Asp Ile Asp Ala
        35                  40                  45

Thr Cys Thr Pro Arg Arg Ala Ser Ser Asn Gln Arg Gly Leu Asn Gln
    50                  55                  60

Ile Trp Asn Val Lys Lys Gln Ser Val Tyr Leu Met Asn Leu Arg Lys
65                  70                  75                  80

Ser Gly Thr Leu Gly His Pro Gly Ser Leu Asp Glu Thr Thr Tyr Glu
                85                  90                  95

Arg Leu Ala Glu Glu Thr Leu Asp Ser Leu Ala Glu Phe Phe Glu Asp
            100                 105                 110

Leu Ala Asp Lys Pro Tyr Thr Phe Glu Asp Tyr Asp Val Ser Phe Gly
        115                 120                 125

Ser Gly Val Leu Thr Val Lys Leu Gly Gly Asp Leu Gly Thr Tyr Val
    130                 135                 140

Ile Asn Lys Gln Thr Pro Asn Lys Gln Ile Trp Leu Ser Ser Pro Ser
145                 150                 155                 160

Ser Gly Pro Lys Arg Tyr Asp Trp Thr Gly Lys Asn Trp Val Tyr Ser
                165                 170                 175

His Asp Gly Val Ser Leu His Glu Leu Leu Ala Ala Glu Leu Thr Lys
            180                 185                 190

Ala Leu Lys Thr Lys Leu Asp Leu Ser Ser Leu Ala Tyr Ser Gly Lys
        195                 200                 205

Asp Ala
    210

<210> SEQ ID NO 2
<211> LENGTH: 130
<212> TYPE: PRT
<213> ORGANISM: Homo sapiens

<400> SEQUENCE: 2

Ser Gly Thr Leu Gly His Pro Gly Ser Leu Asp Glu Thr Thr Tyr Glu
1               5                   10                  15

Arg Leu Ala Glu Glu Thr Leu Asp Ser Leu Ala Glu Phe Phe Glu Asp
```

-continued

```
                 20                  25                  30

Leu Ala Asp Lys Pro Tyr Thr Phe Glu Asp Tyr Asp Val Ser Phe Gly
            35                  40                  45

Ser Gly Val Leu Thr Val Lys Leu Gly Gly Asp Leu Gly Thr Tyr Val
 50                  55                  60

Ile Asn Lys Gln Thr Pro Asn Lys Gln Ile Trp Leu Ser Ser Pro Ser
 65                  70                  75                  80

Ser Gly Pro Lys Arg Tyr Asp Trp Thr Gly Lys Asn Trp Val Tyr Ser
                 85                  90                  95

His Asp Gly Val Ser Leu His Glu Leu Leu Ala Ala Glu Leu Thr Lys
            100                 105                 110

Ala Leu Lys Thr Lys Leu Asp Leu Ser Ser Leu Ala Tyr Ser Gly Lys
        115                 120                 125

Asp Ala
    130

<210> SEQ ID NO 3
<211> LENGTH: 80
<212> TYPE: PRT
<213> ORGANISM: Homo sapiens

<400> SEQUENCE: 3

Met Trp Thr Leu Gly Arg Arg Ala Val Ala Gly Leu Leu Ala Ser Pro
  1               5                  10                  15

Ser Pro Ala Gln Ala Gln Thr Leu Thr Arg Val Pro Arg Pro Ala Glu
                 20                  25                  30

Leu Ala Pro Leu Cys Gly Arg Arg Gly Leu Arg Thr Asp Ile Asp Ala
            35                  40                  45

Thr Cys Thr Pro Arg Arg Ala Ser Ser Asn Gln Arg Gly Leu Asn Gln
 50                  55                  60

Ile Trp Asn Val Lys Lys Gln Ser Val Tyr Leu Met Asn Leu Arg Lys
 65                  70                  75                  80

<210> SEQ ID NO 4
<211> LENGTH: 11
<212> TYPE: PRT
<213> ORGANISM: Human immunodeficiency virus

<400> SEQUENCE: 4

Tyr Gly Arg Lys Lys Arg Arg Gln Arg Arg Arg
  1               5                  10

<210> SEQ ID NO 5
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Met Tyr Gly Arg Lys Lys Arg Arg Gln Arg Arg Arg
  1               5                  10

<210> SEQ ID NO 6
<211> LENGTH: 30
<212> TYPE: PRT
<213> ORGANISM: Unknown
<220> FEATURE:
<223> OTHER INFORMATION: Description of Unknown:
      Galanin sequence
```

```
<400> SEQUENCE: 6

Gly Trp Thr Leu Asn Ser Ala Gly Tyr Leu Leu Gly Pro His Ala Val
1               5                   10                  15

Gly Asn His Arg Ser Phe Ser Asp Lys Asn Gly Leu Thr Ser
            20                  25                  30

<210> SEQ ID NO 7
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ile Asn Leu Lys Ala Leu Ala Ala Leu Ala Lys Lys Ile Leu
1               5                   10

<210> SEQ ID NO 8
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 9
<211> LENGTH: 16
<212> TYPE: PRT
<213> ORGANISM: Drosophila sp.

<400> SEQUENCE: 9

Arg Gln Ile Lys Ile Trp Phe Gln Asn Arg Arg Met Lys Trp Lys Lys
1               5                   10                  15

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Arg Arg Arg Arg Arg Arg Arg Arg Arg
1               5

<210> SEQ ID NO 11
<211> LENGTH: 34
<212> TYPE: PRT
<213> ORGANISM: Human alphaherpesvirus 1

<400> SEQUENCE: 11

Asp Ala Ala Thr Ala Thr Arg Gly Arg Ser Ala Ala Ser Arg Pro Thr
1               5                   10                  15

Glu Arg Pro Arg Ala Pro Ala Arg Ser Ala Ser Arg Pro Arg Arg Pro
            20                  25                  30
```

-continued

Val Glu

<210> SEQ ID NO 12
<211> LENGTH: 224
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

```
Met Tyr Gly Arg Lys Lys Arg Arg Gln Arg Arg Gly Gly Met Trp
1               5                   10                  15

Thr Leu Gly Arg Arg Ala Val Ala Gly Leu Leu Ala Ser Pro Ser Pro
            20                  25                  30

Ala Gln Ala Gln Thr Leu Thr Arg Val Pro Arg Pro Ala Glu Leu Ala
        35                  40                  45

Pro Leu Cys Gly Arg Arg Gly Leu Arg Thr Asp Ile Asp Ala Thr Cys
    50                  55                  60

Thr Pro Arg Arg Ala Ser Ser Asn Gln Arg Gly Leu Asn Gln Ile Trp
65                  70                  75                  80

Asn Val Lys Lys Gln Ser Val Tyr Leu Met Asn Leu Arg Lys Ser Gly
                85                  90                  95

Thr Leu Gly His Pro Gly Ser Leu Asp Glu Thr Thr Tyr Glu Arg Leu
            100                 105                 110

Ala Glu Glu Thr Leu Asp Ser Leu Ala Glu Phe Phe Glu Asp Leu Ala
            115                 120                 125

Asp Lys Pro Tyr Thr Phe Glu Asp Tyr Asp Val Ser Phe Gly Ser Gly
        130                 135                 140

Val Leu Thr Val Lys Leu Gly Gly Asp Leu Gly Thr Tyr Val Ile Asn
145                 150                 155                 160

Lys Gln Thr Pro Asn Lys Gln Ile Trp Leu Ser Ser Pro Ser Ser Gly
                165                 170                 175

Pro Lys Arg Tyr Asp Trp Thr Gly Lys Asn Trp Val Tyr Ser His Asp
            180                 185                 190

Gly Val Ser Leu His Glu Leu Leu Ala Ala Glu Leu Thr Lys Ala Leu
        195                 200                 205

Lys Thr Lys Leu Asp Leu Ser Ser Leu Ala Tyr Ser Gly Lys Asp Ala
    210                 215                 220
```

METHODS FOR QUANTIFYING FRATAXIN ACTIVITY

RELATED APPLICATIONS

This application claims priority to U.S. Provisional Patent Application No. 62/940,214, filed on Nov. 25, 2019, the entire contents of which are hereby incorporated herein by reference.

SEQUENCE LISTING

The instant application contains a Sequence Listing which has been submitted electronically in ASCII format and is hereby incorporated by reference in its entirety. Said ASCII copy, created on Nov. 24, 2020, is named 130197-01002_SL.txt and is 8,325 bytes in size.

INTRODUCTION

Friedreich's Ataxia (FRDA) is a rare genetic, progressive neurodegenerative disorder caused by a mutation in a gene encoding frataxin (FXN). FXN is an essential and phylogenetically conserved protein that is found in cells throughout the body, with the highest levels in the heart, spinal cord, liver, pancreas, and skeletal muscle. FXN is encoded in the nucleus, expressed in the cytoplasm and imported into the mitochondria where it is processed to the mature form. In humans, the 210-amino acid full-length hFXN (hFXN$_{1-210}$, 23.1 kDa) contains a typical mitochondrial targeting sequence (MTS) at the amino terminus that is processed in a 2-step cleavage by the mitochondrial matrix processing peptidase (MPP) as it is imported into the mitochondrial matrix. The resulting protein is a 130-amino acid, 14.2 kDa mature hFXN protein (hFXN$_{81-210}$).

An FXN fusion protein is currently under investigation as an FXN replacement therapy to restore functional levels of FXN in the mitochondria of FRDA patients. The FXN fusion protein includes the HIV-TAT peptide linked to the N-terminus of the full-length hFXN protein. The mechanism of action of the FXN fusion protein relies on the cell-penetrating ability of the HIV-TAT peptide to deliver the FXN fusion protein into cells and the subsequent processing into mature hFXN after translocation into the mitochondria. The FXN fusion protein is described in U.S. Provisional Patent Application No. 62/891,029 and U.S. patent application Ser. No. 16/942,276, the entire contents of each of which are hereby incorporated herein by reference.

To facilitate development of FXN replacement therapies, methods are needed to accurately and reliably quantify activity of FXN and FXN fusion proteins. For example, it is desirable to quantify activity of various batches of FXN fusion proteins, as a quality control measure of the manufacturing process for producing the FXN fusion proteins. It is also desirable to quantify activity of various batches of FXN fusion proteins to identify appropriate storage conditions for the manufactured batches of FXN fusion proteins. The present invention addresses this unmet need.

SUMMARY OF THE INVENTION

Accordingly, in some aspects the present disclosure provides a method for measuring activity of a Frataxin (FXN) protein, the method comprising: combining the FXN protein with a reducing agent and a reactive oxygen species (ROS) detector compound, thereby producing an assay mixture, wherein the FXN protein facilitates oxidation of the reducing agent and generation of ROS, such that the amount of ROS generated is higher than the amount of ROS generated in an assay mixture comprising the reducing agent and the ROS detector compound without the FXN protein.

In some aspects, the present disclosure provides a method for measuring activity of a Frataxin (FXN) protein, the method comprising combining the FXN protein with a reducing agent and a reactive oxygen species (ROS) detector compound at a pH of greater than about 7.4, thereby producing an assay mixture, wherein the FXN protein facilitates oxidation of the reducing agent and generation of ROS, such that the amount of ROS generated is higher than the amount of ROS generated in an assay mixture comprising the reducing agent and the ROS detector compound without the FXN protein.

In some embodiments, the method comprises combining the FXN protein with a reducing agent and a reactive oxygen species (ROS) detector compound at a pH of about 7.9 or greater.

In some aspects, the present disclosure provides a method for measuring activity of a Frataxin (FXN) protein, the method comprising combining the FXN protein with a reducing agent and a reactive oxygen species (ROS) detector compound in the absence of metal ions, thereby producing an assay mixture, wherein the FXN protein facilitates oxidation of the reducing agent and generation of ROS, such that the amount of ROS generated is higher than the amount of ROS generated in an assay mixture comprising the reducing agent and the ROS detector compound without the FXN protein.

In some aspects, the present disclosure provides a method for measuring activity of a Frataxin (FXN) protein, the method comprising combining the FXN protein with a reducing agent and a reactive oxygen species (ROS) detector compound in the absence of iron ions, thereby producing an assay mixture, wherein the FXN protein facilitates oxidation of the reducing agent and generation of ROS, such that the amount of ROS generated is higher than the amount of ROS generated in an assay mixture comprising the reducing agent and the ROS detector compound without the FXN protein.

In some embodiments, the method further comprises adjusting pH of the assay mixture to pH of greater than about 7.4. In some embodiments, the method further comprises adjusting pH of the assay mixture to pH of about 7.9 or greater.

In some embodiments, the method further comprises adding a metal ion into the assay mixture. In some embodiments, the metal ion is not $Fe^{2+}$. In some embodiments, the metal ion is selected from the group consisting of $Mn^{2+}$, $Fe^{3+}$, $Zn^{2+}$, $Cu^{2+}$ and $Mg^{2+}$. In one embodiment, the metal ion is $Mn^{2+}$. In another embodiment, the metal is $Fe^{3+}$.

In some embodiments, the method further comprises incubating the assay mixture. In some embodiments, the method further comprises measuring the amount of ROS generated in the assay mixture. In some embodiments, the method further comprises measuring the amount of ROS generated in the assay mixture over time.

In some embodiments, the method further comprises measuring the amount of ROS generated at regular time intervals. In some embodiments, the method comprises measuring the amount of ROS generated about every 0.1 second to about every 10 minutes, e.g., about every 0.1 second to about every 2 seconds, about every 1 second to about every 10 seconds, about every 5 seconds to about every 60 seconds, about every 30 seconds to about every 5 minutes or about every 2 minutes to about every 10 minutes after the start of incubation of the assay mixture.

In some embodiments, the method further comprises determining maximum initial velocity (Vi) of ROS generation in the assay mixture. In some embodiments, the method further comprises determining time to maximum initial velocity (Ti). In some embodiments, the method further comprises determining the unit activity of the FXN protein at pH of greater than about 7.4.

In some aspects, the present disclosure provides a method for measuring activity of a Frataxin (FXN) protein, the method comprising combining the FXN protein with a reducing agent and a reactive oxygen species (ROS) detector compound, thereby producing an assay mixture; and measuring the amount of ROS generated in the assay mixture over time, wherein the FXN protein facilitates oxidation of the reducing agent and generation of ROS, such that the amount of ROS generated is higher than the amount of ROS generated in an assay mixture comprising a reducing agent and an ROS detector compound without the FXN protein.

In some embodiments, the method comprises measuring the amount of ROS generated at regular time intervals. In some embodiments, the method comprises measuring the amount of ROS generated about every 0.1 second to about every 10 minutes, e.g., about every 0.1 second to about every 2 seconds, about every 1 second to about every 10 seconds, about every 5 seconds to about every 60 seconds, about every 30 seconds to about every 5 minutes or about every 2 minutes to about every 10 minutes.

In some embodiments, the method further comprises determining maximum initial velocity (Vi) of ROS generation in the assay mixture. In some embodiments, the method further comprises determining time to maximum initial velocity (Ti). In some embodiments, the method further comprises determining the unit activity of the FXN protein.

In some embodiments, the reducing agent is an organic compound. In some embodiments, the reducing agent is a reduced quinone compound. In some embodiments, the reduced quinone compound is selected from the group consisting of a reduced benzoquinone compound, a reduced naphthoquinone compound and reduced anthraquinone compound. In some embodiments, the reduced quinone compound is a reduced benzoquinone compound. In some embodiments, the reduced benzoquinone compound is hydroquinone.

In some embodiments, the ROS detector compound is a fluorescent probe or a chemiluminescent probe. In some embodiments, the ROS detector compound is a superoxide anion detection reagent or a hydrogen peroxide detection reagent. In some embodiments, the ROS detector compound is selected from the group consisting of coelenterazine; dihydroethidium; 2',7'-dichlorodihydrofluorescein (H2DCF), lucigenin, luminol, Cypridina Luciferin Analog (CLA), Cypridina Luciferin methoxy-analogue (MCLA), methylthiazolyldiphenyl-tetrazolium bromide (MTT), p-nitrotetrazolium blue (NBT), RedoxSensor Red CC-1, 2,3-Bis-(2-Methoxy-4-Nitro-5-Sulfophenyl)-2H-Tetrazolium-5-Carboxanilide (XTT) and structural variants and analogs thereof. In some embodiments, the ROS detector compound is 2',7'-dichlorodihydrofluorescein diacetate ($H_2DCF$).

In some embodiments, the reducing agent and the ROS detector compound are the same compound. In some embodiments, the reducing agent and the ROS detector compound are different compounds. In one embodiment, the reducing agent is dihydroquinone and the ROS detector compound is 2',7'-dichlorodihydrofluorescein (H2DCF).

In some embodiments, the FXN protein is frataxin (FXN). In some embodiments, the FXN protein is an FXN fusion protein comprising full-length hFXN and a cell penetrating peptide (CPP). In some embodiments, the CPP comprises a peptide selected from the group of CPPs listed in the Database of Cell-Penetrating Peptides CPPsite 2.0. In some embodiments, the CPP comprises a peptide selected from the group consisting of HIV-TAT, galanin, mastoparan, transportan, penetratin, polyarginine, VP22, and a variant or derivative thereof.

In some embodiments, the CPP comprises HIV-TAT or a variant or derivative thereof. In one embodiment, the FXN fusion protein comprises SEQ ID NO: 12.

In some aspects, the present disclosure provides a method for performing quality control on a sample comprising a Frataxin (FXN) protein, the method comprising measuring activity of an FXN protein in accordance with methods of the disclosure.

In some aspects, the present disclosure provides a composition for measuring activity of an FXN protein, the composition comprising an FXN protein, a reducing agent and a reactive oxygen species (ROS) detector compound, wherein pH of the composition is greater than about 7.4. In some embodiments, pH of the composition is about 7.9 or greater.

In some embodiments, the composition further comprises a metal ion. In some embodiments, the metal ion is not $Fe^{2+}$. In some embodiments, the metal ion is selected from the group consisting of $Mn^{2+}$, $Fe^{3+}$, $Zn^{2+}$, $Cu^{2+}$ and $Mg^{2+}$. In one embodiment, the metal ion is $Fe^{3+}$. In another embodiment, the metal ion is $Mn^{2+}$.

In some aspects, the present disclosure also provides a composition for measuring activity of an FXN protein, the composition comprising an FXN protein, a reducing agent and a reactive oxygen species (ROS) detector compound, wherein the composition is substantially free of a metal ions.

In some aspects, the present disclosure also provides a composition for measuring activity of an FXN protein, the composition comprising an FXN protein, a reducing agent and a reactive oxygen species (ROS) detector compound, wherein the composition is substantially free of iron ions.

In some embodiments, pH of the composition is greater than about 7.4. In some embodiments, pH of the composition is about 7.9 or greater.

In some embodiments, the reducing agent is an organic compound. In some embodiments, the reducing agent is a reduced quinone compound. In some embodiments, the reduced quinone compound is selected from the group consisting of a reduced benzoquinone compound, a reduced naphthoquinone compound and a reduced anthraquinone compound. In some embodiments, the reduced quinone compound is a reduced benzoquinone compound. In some embodiments, the reduced benzoquinone compound is hydroquinone.

In some embodiments, the ROS detector compound is a fluorescent probe or a chemiluminescent probe. In some embodiments, the ROS detector compound is a superoxide anion detection reagent or a hydrogen peroxide detection reagent. In some embodiments, the ROS detector compound is selected from the group consisting of coelenterazine; dihydroethidium; 2',7'-dichlorodihydrofluorescein (H2DCF), lucigenin, luminol, Cypridina Luciferin Analog (CLA), Cypridina Luciferin methoxy-analogue (MCLA), methylthiazolyldiphenyl-tetrazolium bromide (MTT), p-nitrotetrazolium blue (NBT), RedoxSensor Red CC-1, 2,3-Bis-(2-Methoxy-4-Nitro-5-Sulfophenyl)-2H-Tetrazolium-5-Carboxanilide (XTT) and structural variants and analogs thereof. In some embodiments, the ROS detector compound is 2',7'-dichlorodihydrofluorescein ($H_2DCF$).

In some embodiments, the ROS detector compound are the same compound. In some embodiments, the reducing agent and the ROS detector compound are different compounds. In one embodiment, the reducing agent is dihydroquinone and the ROS detector compound is 2',7'-dichloro-dihydrofluorescein ($H_2DCF$).

In some embodiments, the FXN protein is frataxin (FXN). In some embodiments, the FXN protein is an FXN fusion protein comprising full-length hFXN and a cell penetrating peptide (CPP). In some embodiments, the CPP comprises a peptide selected from the group of CPPs listed in the Database of Cell-Penetrating Peptides CPPsite 2.0. In some embodiments, the CPP comprises a peptide selected from the group consisting of HIV-TAT, galanin, mastoparan, transportan, penetratin, polyarginine, VP22, and a variant or derivative thereof.

In some embodiments, the CPP comprises HIV-TAT or a variant or derivative thereof. In some embodiments, the FXN fusion protein comprises SEQ ID NO: 12.

In some aspects, the present disclosure also provides a composition comprising an FXN protein, wherein the FXN protein exhibits a specific activity of hydroquinone reduction within the range of about 1000 mU/mg of FXN protein to about 6500 mU/mg of FXN protein. In some embodiments, the specific activity of hydroquinone reduction is within the range of about 1200 mU/mg to about 6000 mU/mg. In some embodiments, the specific activity is within the range of about 1400 mU/mg to about 5900 mU/mg.

In some aspects, the present disclosure also provides a kit for determining activity of an FXN protein, the kit comprising a reducing agent, an ROS detector compound and instructions to combine the reducing agent, the ROS detector compound and an FXN protein, thereby producing an assay mixture.

In some aspects, the present disclosure also provides a kit for determining activity of an FXN protein, the kit comprising a reducing agent, an ROS detector compound and instructions to combine the reducing agent, the ROS detector compound and an FXN protein, thereby producing an assay mixture; and determine Vi of the FXN protein in the assay mixture.

In some embodiments, the kit further comprises a metal ion compound. In some embodiments, the metal ion compound comprises an ion selected from the group consisting of $Mn^{2+}$, $Fe^{3+}$, $Zn^{2+}$, $Cu^{2+}$ and $Mg^{2+}$. In one embodiment, the metal ion compound comprises $Fe^{3+}$. In another embodiment, the metal ion compound comprises $Mn^{2+}$.

In some embodiments, the reducing agent is an organic compound. In some embodiments, the reducing agent is a reduced quinone compound. In some embodiments, the reduced quinone compound is selected from the group consisting of a reduced benzoquinone compound, a reduced naphthoquinone compound and a reduced anthraquinone compound. In some embodiments, the reduced quinone compound is a reduced benzoquinone compound. In some embodiments, the reduced benzoquinone compound is hydroquinone.

In some embodiments, the ROS detector compound is a fluorescent probe or a chemiluminescent probe. In some embodiments, the ROS detector compound is a superoxide anion detection reagent or a hydrogen peroxide detection reagent. In some embodiments, the ROS detector compound is selected from the group consisting of coelenterazine; dihydroethidium; 2',7'-dichlorodihydrofluorescein (H2DCF), lucigenin, luminol, Cypridina Luciferin Analog (CLA), Cypridina Luciferin methoxy-analogue (MCLA), methylthiazolyldiphenyl-tetrazolium bromide (MTT), p-nitrotetrazolium blue (NBT), RedoxSensor Red CC-1, 2,3-Bis-(2-Methoxy-4-Nitro-5-Sulfophenyl)-2H-Tetrazolium-5-Carboxanilide (XTT) and structural variants and analogs thereof. In some embodiments, the ROS detector compound is 2',7'-dichlorodihydrofluorescein ($H_2DCF$).

In some embodiments, the reducing agent and the ROS detector compound are the same compound. In some embodiments, the reducing agent and the ROS detector compound are different compounds. In some embodiments, the reducing agent is dihydroquinone and the ROS detector compound is 2',7'-dichlorodihydrofluorescein ($H_2DCF$).

In some aspects, the present disclosure also provides a method for identifying a compound capable of modulating activity of a Frataxin (FXN) protein, the method comprising the steps of: (i) combining the FXN protein with a test compound, a reducing agent and a reactive oxygen species (ROS) detector compound, thereby producing an assay mixture, wherein the FXN protein facilitates oxidation of the reducing agent and generation of ROS; (ii) measuring the amount of ROS generated in the presence of the test compound; (iii) comparing the amount of ROS generated in the presence of the test compound with an amount of ROS generated in the absence of the test compound; and (iv) identifying the test compound as a compound capable of modulating activity of the FXN protein when the amount of ROS generated in the presence of the test compound is different from the amount of ROS generated in the absence of the test compound.

In some embodiments, the method further comprises incubating the assay mixture. In some embodiments, step (ii) comprises measuring the amount of ROS generated in the assay mixture over time. In some embodiments, step (ii) comprises measuring the amount of ROS generated at regular time intervals. In some embodiments, step (ii) comprises measuring the amount of ROS generated every 0.1 second to every 10 minutes, e.g., about every 0.1 second to about every 2 seconds, about every 1 second to about every 10 seconds, about every 5 seconds to about every 60 seconds, about every 30 seconds to about every 5 minutes or about every 2 minutes to about every 10 minutes.

In some embodiments, the method further comprises determining maximum initial velocity (Vi) of ROS generation in the assay mixture. In some embodiments, the method further comprises determining time to maximum initial velocity (Ti). In some embodiments, the method further comprises determining the unit activity of the FXN protein.

In some embodiments, the method further comprises the steps of: comparing Vi of the FXN protein in the presence of the test compound with Vi of the FXN protein in the absence of the test compound; and identifying the test compound as a compound capable of modulating activity of the FXN protein when the Vi of the FXN protein in the presence of the test compound is different from the Vi of the FXN protein in the absence of the test compound.

In some aspects, the present disclosure comprises identifying a compound capable of modulating activity of a Frataxin (FXN) protein, the method comprising the steps of: (i) combining the FXN protein with a test compound, a reducing agent and a reactive oxygen species (ROS) detector compound, thereby producing an assay mixture, wherein the FXN protein facilitates oxidation of the reducing agent and generation of ROS; (ii) measuring the amount of ROS generated in the presence of the test compound and determining Vi of the FXN protein; (iii) comparing the Vi of the FXN protein in the presence of the test compound with Vi of the FXN protein in the absence of the test compound; and (iv) identifying the test compound as a compound capable of modulating activity of the FXN protein when Vi of the FXN protein in the presence of the test compound is different from Vi of the FXN protein in the absence of the test compound.

In some embodiments, the method further comprises adjusting pH of the assay mixture to pH of greater than about 7.4. In some embodiments, the method further comprises adjusting pH of the assay mixture to pH of about 7.9 or greater.

In some embodiments, the method further comprises adding a metal ion to the assay mixture. In some embodiments, the metal ion is selected from the group consisting of $Mn^{2+}$, $Fe^{3+}$, $Zn^{2+}$, $Cu^{2+}$ and $Mg^{2+}$. In one embodiment, the metal ion is $Mn^{2+}$. In another embodiment, the metal ion is $Fe^{3+}$.

In some embodiments, the reducing agent is an organic compound. In some embodiments, the reducing agent is a reduced quinone compound. In some embodiments, the reduced quinone compound is selected from the group consisting of a reduced benzoquinone compound, a reduced naphthoquinone compound and reduced anthraquinone compound. In some embodiments, the reduced quinone compound is a reduced benzoquinone compound. In some embodiments, the reduced benzoquinone compound is hydroquinone.

In some embodiments, the ROS detector compound is a fluorescent probe or a chemiluminescent probe. In some embodiments, the ROS detector compound is a superoxide anion detection reagent or a hydrogen peroxide detection reagent. In some embodiments, the ROS detector compound is selected from the group consisting of coelenterazine; dihydroethidium; 2',7'-dichlorodihydrofluorescein ($H_2DCF$), lucigenin, luminol, Cypridina Luciferin Analog (CLA), Cypridina Luciferin methoxy-analogue (MCLA), methylthiazolyldiphenyl-tetrazolium bromide (MTT), p-nitrotetrazolium blue (NBT), RedoxSensor Red CC-1, 2,3-Bis-(2-Methoxy-4-Nitro-5-Sulfophenyl)-2H-Tetrazolium-5-Carboxanilide (XTT) and structural variants and analogs thereof. In some embodiments, the ROS detector compound is 2',7'-dichlorodihydrofluorescein ($H_2DCF$).

In some embodiments, the reducing agent and the ROS detector compound are the same compound. In some embodiments, the reducing agent and the ROS detector compound are different compounds. In one embodiment, the reducing agent is dihydroquinone and the ROS detector compound is 2',7'-dichlorodihydrofluorescein ($H_2DCF$).

In some embodiments, the FXN protein is frataxin (FXN). In some embodiments, the FXN protein is an FXN fusion protein comprising full-length hFXN and a cell penetrating peptide (CPP). In some embodiments, the CPP comprises a peptide selected from the group of CPPs listed in the Database of Cell-Penetrating Peptides CPPsite 2.0. In some embodiments, the CPP comprises a peptide selected from the group consisting of HIV-TAT, galanin, mastoparan, transportan, penetratin, polyarginine, VP22, and a variant or derivative thereof.

In some embodiments, the CPP comprises HIV-TAT or a variant or derivative thereof. In some embodiments, the FXN fusion protein comprises SEQ ID NO: 12.

In some aspects, the present disclosure also provides a composition comprising an FXN protein, wherein activity of the FXN protein has been measured according to the methods of the present disclosure.

In some aspects, the present disclosure provides a pharmaceutical composition comprising an FXN protein and a pharmaceutically acceptable excipient, wherein activity of the FXN protein has been measured according to the method of the present disclosure.

In some aspects, the present disclosure provides a method of preparing a pharmaceutical composition comprising an FXN protein, the method comprising measuring activity of the FXN protein according to the method of the present disclosure, and formulating the FXN protein, thereby preparing the pharmaceutical composition.

In some embodiments, the present disclosure provides a method for measuring activity of a Frataxin (FXN) protein, the method comprising combining the FXN protein with a reducing agent and a reactive oxygen species (ROS) detector compound, thereby producing an assay mixture, wherein the FXN protein facilitates oxidation of the reducing agent and generation of ROS.

In some embodiments, the method further comprises adding a metal ion into the assay mixture. In further aspects, the metal ion is selected from the group consisting of $Mn^{2+}$, $Fe^{3+}$, $Zn^{2+}$, $Cu^{2+}$ and $Mg^{2+}$. In one further aspect, the metal ion is $Fe^{3+}$. In another further aspect, the metal ion is $Mn^{2+}$.

In some embodiments, the method further comprises incubating the assay mixture. In some embodiments, the method further comprises measuring the amount of ROS generated. In some embodiments, the method further comprises correlating the amount of ROS generated with activity of the FXN protein, thereby determining the activity the FXN protein.

In some aspects, the reducing agent is an organic compound. In some aspects, the reducing agent is a reduced quinone compound. In some aspects, the reduced quinone compound is selected from the group consisting of a reduced benzoquinone compound, a reduced naphthoquinone compound and reduced anthraquinone compound. In some embodiments, the reduced quinone compound is a reduced benzoquinone compound. In one embodiment, the reduced benzoquinone compound is hydroquinone.

In some aspects, the ROS detector compound is a fluorescent probe or a chemiluminescent probe. In some aspects, the ROS detector compound is a superoxide anion detection reagent or a hydrogen peroxide detection reagent. In some embodiments, the ROS detector compound is selected from the group consisting of coelenterazine; dihydroethidium; 2',7'-dichlorodihydrofluorescein ($H_2DCF$), lucigenin, luminol, Cypridina Luciferin Analog (CLA), Cypridina Luciferin methoxy-analogue (MCLA), methylthiazolyldiphenyl-tetrazolium bromide (MTT), p-nitrotetrazolium blue (NBT), RedoxSensor Red CC-1, 2,3-Bis-(2-Methoxy-4-Nitro-5-Sulfophenyl)-2H-Tetrazolium-5-Carboxanilide (XTT) and structural variants and analogs thereof. In one specific embodiment, the ROS detector compound is 2',7'-dichlorodihydrofluorescein diacetate ($H_2DCF$).

In some embodiments, the reducing agent and the ROS detector compound are the same compound. In other embodiments, the reducing agent and the ROS detector compound are different compounds.

In some embodiments, the reducing agent is dihydroquinone and the ROS detector compound is 2',7'-dichlorodihydrofluorescein ($H_2DCF$).

In some aspects, the FXN protein is frataxin (FXN). In some aspects, the FXN protein is an FXN fusion protein comprising full-length hFXN and a cell penetrating peptide (CPP).

In some embodiments, the CPP comprises a peptide selected from the group of CPPs listed in the Database of Cell-Penetrating Peptides CPPsite 2.0. In some embodiments, the CPP comprises a peptide selected from the group consisting of HIV-TAT, galanin, mastoparan, transportan, penetratin, polyarginine, VP22, and a variant or derivative thereof. In one aspect, the CPP comprises HIV-TAT or a variant or derivative thereof.

In some embodiments, the FXN fusion protein comprises, or consists of, SEQ ID NO: 12.

In some embodiments, the present disclosure provides a method of performing quality control on a sample comprising a Frataxin (FXN) protein, the method comprising measuring activity of an FXN protein in accordance with the methods of the present disclosure.

In some embodiments, the present invention provides a composition for measuring activity of an FXN protein, the composition comprising an FXN protein, a reducing agent and a reactive oxygen species (ROS) detector compound.

In some aspects, the composition further comprises a metal ion. In some aspects, the metal ion is selected from the group consisting of $Mn^{2+}$, $Fe^{3+}$, $Zn^{2+}$, $Cu^{2+}$ and $Mg^{2+}$. In one further aspect, the metal ion is $Fe^{2+}$. In another further aspect, the metal ion is $Mn^{2+}$.

In some embodiments, the reducing agent is an organic compound. In some embodiments, the reducing agent is a reduced quinone compound. In some aspects, the reduced quinone compound is selected from the group consisting of a reduced benzoquinone compound, a reduced naphthoquinone compound and a reduced anthraquinone compound.

In some aspects, the reduced quinone compound is a reduced benzoquinone compound. In one aspect, the reduced benzoquinone compound is hydroquinone.

In some embodiments, the ROS detector compound is a fluorescent probe or a chemiluminescent probe. In some embodiments, the ROS detector compound is a superoxide anion detection reagent or a hydrogen peroxide detection reagent. In some embodiments, the ROS detector compound is selected from the group consisting of coelenterazine; dihydroethidium; 2',7'-dichlorodihydrofluorescein ($H_2DCF$), lucigenin, luminol, Cypridina Luciferin Analog (CLA), Cypridina Luciferin methoxy-analogue (MCLA), methylthiazolyldiphenyl-tetrazolium bromide (MTT), p-nitrotetrazolium blue (NBT), RedoxSensor Red CC-1, 2,3-Bis-(2-Methoxy-4-Nitro-5-Sulfophenyl)-2H-Tetrazolium-5-Carboxanilide (XTT) and structural variants and analogs thereof. In one embodiment, the ROS detector compound is 2',7'-dichlorodihydrofluorescein ($H_2DCF$).

In some aspects, the reducing agent and the ROS detector compound are the same compound. In other aspects, the reducing agent and the ROS detector compound are different compounds. In one aspect, the reducing agent is dihydroquinone and the ROS detector compound is 2',7'-dichlorodihydrofluorescein ($H_2DCF$).

In some embodiments, the FXN protein is frataxin (FXN). In some embodiments, the FXN protein is an FXN fusion protein comprising full-length hFXN and a cell penetrating peptide (CPP). In some aspects, the CPP comprises a peptide selected from the group of CPPs listed in the Database of Cell-Penetrating Peptides CPPsite 2.0. In some aspects, the CPP comprises a peptide selected from the group consisting of HIV-TAT, galanin, mastoparan, transportan, penetratin, polyarginine, VP22, and a variant or derivative thereof. In one embodiment, the CPP comprises HIV-TAT or a variant or derivative thereof.

In one aspect, the FXN fusion protein comprises, or consists of, SEQ ID NO: 12.

In some embodiments, the present disclosure provides a composition comprising an FXN protein, wherein the FXN protein exhibits a specific activity of hydroquinone reduction within the range of about 1000 mU/mg of FXN protein to about 6500 mU/mg of FXN protein. In some embodiments, the specific activity of hydroquinone reduction is within the range of about 1200 mU/mg to about 6000 mU/mg. In some embodiments, the specific activity is within the range of about 1400 mU/mg to about 5900 mU/mg.

In some embodiments, the present disclosure provides a method for identifying a compound capable of modulating activity of a Frataxin (FXN) protein, the method comprising the steps of: (i) combining the FXN protein with a test compound, a reducing agent and a reactive oxygen species (ROS) detector compound, thereby producing an assay mixture, wherein the FXN protein facilitates oxidation of the reducing agent and generation of ROS; (ii) measuring the amount of ROS generated in the presence of the test compound; (iii) comparing the amount of ROS generated in the presence of the test compound with an amount of ROS generated in the absence of the test compound; and (iv) identifying the test compound as a compound capable of modulating activity of the FXN protein when the amount of ROS generated in the presence of the test compound is different from the amount of ROS generated in the absence of the test compound.

In some aspects, the method further comprises incubating the assay mixture. In some aspects, the method further comprises correlating the amount of ROS generated with activity of the FXN protein, thereby determining the activity the FXN protein.

In some embodiments, the reducing agent is an organic compound. In some embodiments, the reducing agent is a reduced quinone compound. In some embodiments, the reduced quinone compound is selected from the group consisting of a reduced benzoquinone compound, a reduced naphthoquinone compound and reduced anthraquinone compound. In some aspects, the reduced quinone compound is a reduced benzoquinone compound. In one aspect, the reduced benzoquinone compound is hydroquinone.

In some embodiments, the ROS detector compound is a fluorescent probe or a chemiluminescent probe. In some embodiments, the ROS detector compound is a superoxide anion detection reagent or a hydrogen peroxide detection reagent. In some embodiments, the ROS detector compound is selected from the group consisting of coelenterazine; dihydroethidium; 2',7'-dichlorodihydrofluorescein ($H_2DCF$), lucigenin, luminol, Cypridina Luciferin Analog (CLA), Cypridina Luciferin methoxy-analogue (MCLA), methylthiazolyldiphenyl-tetrazolium bromide (MTT), p-nitrotetrazolium blue (NBT), RedoxSensor Red CC-1, 2,3-Bis-(2-Methoxy-4-Nitro-5-Sulfophenyl)-2H-Tetrazolium-5-Carboxanilide (XTT) and structural variants and analogs thereof. In one embodiment, the ROS detector compound is 2',7'-dichlorodihydrofluorescein ($H_2DCF$).

In some aspects, the reducing agent and the ROS detector compound are the same compound. In other aspects, the ROS detector compound are different compounds.

In one specific embodiment, the reducing agent is dihydroquinone and the ROS detector compound is 2',7'-dichlorodihydrofluorescein ($H_2DCF$).

In some embodiments, the FXN protein is frataxin (FXN).

In some aspects, the present disclosure also provides a composition comprising an FXN protein, wherein activity of the FXN protein has been measured according to methods provided by the present disclosure.

In some aspects, the present disclosure also provides a pharmaceutical composition comprising an FXN protein and a pharmaceutically acceptable excipient, wherein activity of the FXN protein has been measured according to methods provided of the present disclosure.

In some aspects, the present disclosure also provides a method of preparing a pharmaceutical composition comprising an FXN protein, the method comprising measuring activity of the FXN protein according to methods provided by the present disclosure, and formulating the FXN protein, thereby preparing the pharmaceutical composition.

BRIEF DESCRIPTION OF THE DRAWINGS

Non-limiting examples of embodiments of the disclosure are described below with reference to figures attached hereto that are listed following this paragraph. Identical features that appear in more than one figure are generally labeled with a same label in all the figures in which they appear. A label labeling an icon representing a given feature of an embodiment of the disclosure in a figure may be used to reference the given feature. Dimensions of features shown in the figures are chosen for convenience and clarity of presentation and are not necessarily shown to scale.

FIG. 5 is a bar graph showing the maximum initial velocity (Vi) of superoxide generation in the presence of the FXN fusion protein that has been stored at low and high pH, in the presence of oxidant and at an elevated temperature, in accordance with an embodiment of the disclosure.

DETAILED DESCRIPTION OF THE INVENTION

Figure 1A:
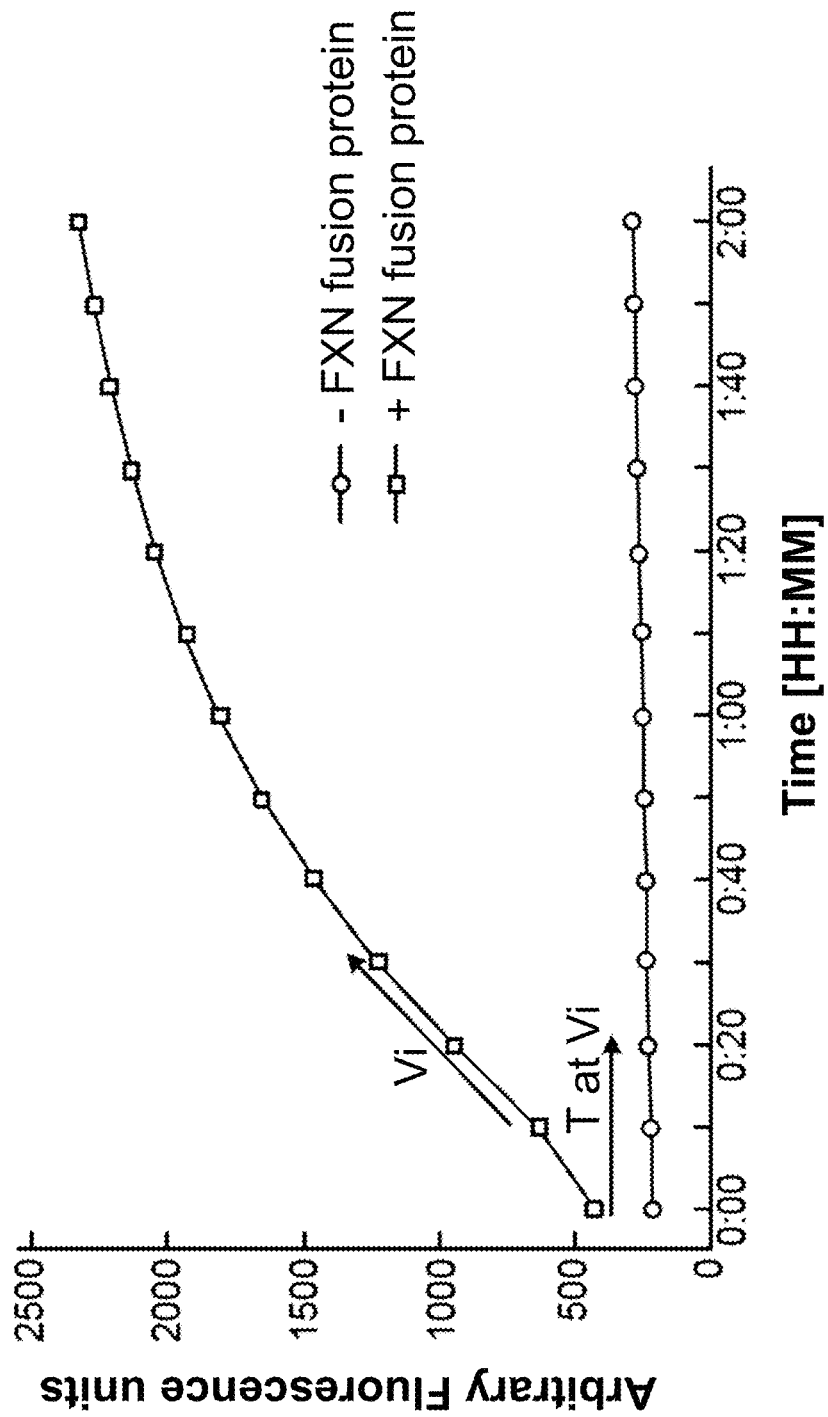
FIG. 1 shows the kinetics of hydroquinone (HQ) reduction in the presence of an exemplary FXN fusion protein, as measured by the amount of reactive oxygen species (ROS) generated over time. The amount of ROS is expressed as fluorescence, measured in arbitrary fluorescence units (AFU). Panel A of FIG. 1 is a graph showing the kinetics of superoxide ($O_2^{\cdot-}$) generation via oxidation of hydroquinone (HQ) in the presence or absence of the FXN fusion protein, in accordance with an embodiment of the disclosure. Panel B of FIG. 1 is a graph showing the kinetics of superoxide generation in the presence of the FXN fusion protein and metal ions, such as $Mn^{2+}$ and $Fe^{3+}$, in accordance with an embodiment of the disclosure. Panel C of FIG. 1 is a graph showing the kinetics of superoxide generation in the presence of the FXN fusion protein and $Fe^{3+}$ (gray squares); in the presence of the FXN fusion protein and in the absence of $Fe^{3+}$ (gray circles); in the presence of the FXN fusion protein, Fe and deferoxamine (black circles); and in the absence of the FXN fusion protein (small black rectangles).

Methods and Compositions for Measuring Activity of an FXN Protein The present disclosure provides methods and compositions for measuring activity of an FXN protein. The present disclosure is based on a surprising discovery that an FXN protein, e.g., FXN fusion protein, such as an exemplary FXN fusion protein having the amino acid sequence of SEQ ID NO: 12, is capable of catalyzing the generation of reactive oxygen species (ROS) and, in particular, superoxide ($O_2^{\cdot-}$), in the presence of a reducing agent. The present disclosure is also based on a surprising discovery that the kinetics of ROS, e.g., superoxide, generation by an FXN protein in the presence of a reducing agent is indicative of an enzymatic reaction. Thus, without wishing to be bound by a specific theory, it is believed that the biological activity of an FXN protein involves enzymatically catalyzed generation of ROS.

The discovery that an FXN protein is capable of catalyzing the generation of ROS, e.g., superoxide, is particularly surprising in view of previous reports in the art that FXN can inhibit production of ROS. In particular, Vyas et al., *Human Molecular Genetics* 2012, 21(6):1230-1247 (hereinafter "Vyas") describes that an FXN fusion protein, TAT-FXN, when mixed with ferrous sulfate and hydroquinone (HQ), inhibits production of superoxide by binding free ferrous and ferric ions and preventing them from participating in an active redox cycle generating superoxide. However, the assay described in Vyas, is a static endpoint assay that does not measure enzymatic activity, and therefore does not measure enzymatic peroxidase activity of an FXN protein. In contrast, the methods for measuring activity of an FXN protein of the present disclosure involve, in some embodiments, kinetic measurements of ROS generation. The methods for measuring activity of an FXN protein of the present disclosure also involve, in some embodiments, identification of enzymatic parameters associated with the ROS generating activity of an FXN protein.

Accordingly, in some embodiments, the present disclosure provides methods for activity of an FXN protein that comprise combining the FXN protein with a reducing agent and a reactive oxygen species (ROS) detector compound, thereby producing an assay mixture, wherein the FXN protein facilitates oxidation of the reducing agent and generation of ROS, such that the amount of ROS generated is higher than the amount of ROS generated in an assay mixture comprising the reducing agent and the ROS detector compound without the FXN protein.

In some embodiments, the present disclosure also provides methods for measuring activity of an FXN protein that comprise combining the FXN protein with a reducing agent and an ROS detector compound, thereby producing an assay mixture; and measuring the amount of ROS generated in the assay mixture over time, wherein the FXN protein facilitates oxidation of the reducing agent and generation of ROS, such that the amount of ROS generated is greater than the amount of ROS generated in an assay mixture comprising a reducing agent and an ROS detector compound without the FXN protein.

In some embodiments, the present disclosure also provides methods for measuring activity of an FXN protein that comprise combining the FXN protein with a reducing agent and an ROS detector compound, thereby producing an assay mixture; and determining maximum initial velocity (Vi) of the FXN protein. The term "maximum initial velocity" or "Vi", as used herein, refers to the rate of the fastest change in arbitrary fluorescence unit (AFU) over time.

In some embodiments, the methods of the present disclosure also comprise determining time to maximum initial velocity (Ti), i.e., the time that it takes for the assay mixture to reach the maximum initial velocity.

In some embodiments, the methods of the disclosure also comprise determining the unit activity of the FXN protein, e.g., milliunit activity of the FXN protein. The term "milliunit activity of the FXN protein", as used herein, is defined as the amount of the FXN protein necessary to catalyze the generation of 1 micromole of 2',7'-dichlorofluorescein (DCF) per minute at a pH of greater than about 7.4, e.g., pH of about 7.9.

The assay described in Vyas requires the presence of $Fe^{2+}$. In contrast, methods for measuring activity of an FXN protein provided by the present disclosure may be carried out either in the absence or in the presence of metal ions. It has been surprisingly discovered that the presence of metal ions is not required for the ROS-generating activity of an FXN protein, but that metal ions, such as Fe and $Mn^{2+}$, enhance the ROS-generating activity of an FXN protein. Without wishing to be bound by a specific theory, it is believed that metal ions may bind to the FXN protein and stabilize its conformation, thereby leading to an enhancement of its ROS generating activity.

Accordingly, in some embodiments, the present disclosure provides methods for measuring activity of an FXN protein that comprise combining the FXN protein with a reducing agent and a reactive oxygen species (ROS) detector compound in the absence of metal ions, thereby producing an assay mixture, wherein the FXN protein facilitates oxidation of the reducing agent and generation of ROS, such that the amount of ROS generated is higher than the amount of ROS generated in an assay mixture comprising the reducing agent and the ROS detector compound without the FXN protein. In some embodiments, the present disclosure also provides methods for measuring activity of an FXN protein that comprise combining the FXN protein with a reducing agent and a reactive oxygen species (ROS) detector compound in the absence of iron ions, thereby producing an assay mixture, wherein the FXN protein facilitates oxidation of the reducing agent and generation of ROS, such that the amount of ROS generated is higher than the amount of ROS generated in an assay mixture comprising the reducing agent and the ROS detector compound without the FXN protein. In some embodiments, iron ions may be $Fe^{2+}$ and/or $Fe^{3+}$.

Accordingly, in some embodiments, the present disclosure provides methods for measuring activity of an FXN protein that comprise combining the FXN protein with a reducing agent and a reactive oxygen species (ROS) detector compound, thereby producing an assay mixture, wherein the FXN protein facilitates oxidation of the reducing agent and generation of ROS, such that the amount of ROS generated is higher than the amount of ROS generated in an assay mixture comprising the reducing agent and the ROS detector compound without the FXN protein, and wherein the oxidation of the reducing agent and generation of ROS is capable of proceeding in the absence of metal ions. In some embodiments, the present disclosure also provides methods for measuring activity of an FXN protein that comprise combining the FXN protein with a reducing agent and a reactive oxygen species (ROS) detector compound, thereby producing an assay mixture, wherein the FXN protein facilitates oxidation of the reducing agent and generation of ROS, such that the amount of ROS generated is higher than the amount of ROS generated in an assay mixture comprising the reducing agent and the ROS detector compound without the FXN protein and wherein the oxidation of the reducing agent and generation of ROS is capable of proceeding in the absence of iron ions. In some embodiments, iron ions may be $Fe^{2+}$ and/or $Fe^{3+}$.

The term "in the absence of metal ions", as used herein, refers to measuring activity of an FXN protein without adding metal ions, e.g., $Fe^{3+}$ or $Mg^{2+}$, to the assay mixture. In some embodiments, this term encompasses measuring activity of an FXN protein in an assay mixture that does not contain added metal ions, but which, nevertheless, may contain trace amounts of metal ions. In some embodiments, the metal ions may be one or more of $Mn^{2+}$, $Fe^{3+}$, $Fe^{2+}$, $Zn^{2+}$, $Cu^{2+}$ and $Mg^{2+}$.

The term "in the absence of iron ions", as used herein, refers to measuring activity of an FXN protein without adding iron ions, e.g., $Fe^{2+}$, $Fe^{3+}$, or $Mn^{2+}$, to the assay mixture. In some embodiments, this term encompasses measuring activity of an FXN protein in an assay mixture that does not contain added iron ions, but which, nevertheless, may contain trace amounts of iron ions. In some embodiments, the assay mixture may contain trace amounts of iron ions, e.g., $Fe^{2+}$ and/or $Fe^{3+}$ ions and/or $Mn^{2+}$. The term "trace amount of metal ions" or "trace amount of a metal ion", in some embodiments, refers to a very low amount of a metal ion, e.g., less than about 0.2 parts per million (ppm), e.g., less than about 0.1 ppm, less than about 0.05 ppm or less than about 0.01 ppm, or less than about 0.05-0.2 ppm. In some embodiments, the term "trace amount of metal ions" or "trace amount of a metal ion" refers to or less than about 100 μg of a metal ion per liter of the assay mixture. In some embodiments, the metal ions may be one or more of $Mn^{2+}$, $Fe^{3+}$, $Fe^{2+}$, $Zn^{2+}$, $Cu^{2+}$ and $Mg^{2+}$.

In some embodiments, the present disclosure also provides a composition for measuring activity of an FXN protein that comprises an FXN protein, a reducing agent and a reactive oxygen species (ROS) detector compound, wherein the composition is substantially free of a metal ions. In some embodiments, the present disclosure provides a composition for measuring activity of an FXN protein that comprises an FXN protein, a reducing agent and a reactive oxygen species (ROS) detector compound, wherein the composition is substantially free of iron ions.

The term "substantially free of metal ions", as used herein, refers to a composition to which metal ions have not been added. In some embodiments, a composition that is substantially free of metal ions may comprise trace amounts of metal ions. The term "substantially free of iron ions", as used herein, refers to a composition to which iron ions have not been added. In some embodiments, a composition that is substantially free of metal ions may comprise trace amounts of iron ions, e.g., $Fe^{2+}$ and/or $Fe^{3+}$.

The assay described in Vyas was carried out in PBS, which typically has a pH of about 7.4. In contrast to the assay described in Vyas, it was surprisingly discovered that activity of an FXN protein, as measured using methods of the present disclosure, is low or absent at the pH of about 7.4. As described in Example 7 and illustrated in FIG. 7, the activity of an FXN protein is pH dependent, and increases from the low or absent levels at pH of about 7.4 to peak at pH of about 8.5. Without wishing to be bound by a specific theory, it is believed that the increased activity of an FXN protein at a pH of greater than about 7.4, as compared to activity at a pH of about 7.4, reflects the fact that FXN is a mitochondrial protein that acts within a mitochondrial matrix having a pH of about 7.8.

Accordingly, in some embodiments, the present disclosure provides methods for measuring activity of a Frataxin (FXN) protein that comprise combining the FXN protein with a reducing agent and a reactive oxygen species (ROS) detector compound at a pH of greater than about 7.4, thereby producing an assay mixture, wherein the FXN protein facilitates oxidation of the reducing agent and generation of ROS, such that the amount of ROS generated is higher than the amount of ROS generated in an assay mixture comprising the reducing agent and the ROS detector compound without the FXN protein. In some embodiments, the FXN protein may be combined with a reducing agent and an ROS detector compound at a pH of greater than about 7.5, greater than about 7.6, greater than about 7.7, greater than about 7.8, greater than about 7.9, greater than about 8.0, greater than about 8.1, greater than about 8.2, greater than about 8.3, greater than about 8.4, greater than about 8.5, greater than about 8.6, greater than about 8.7, greater than about 8.8, greater than about 8.9, or greater than about 9.0. In one embodiment, the pH may be greater than about 7.9.

In some embodiments, the FXN protein may be combined with a reducing agent and an ROS detector compound at a pH of about 7.5 or greater, about 7.6 or greater, about 7.7 or greater, about 7.8 or greater, about 7.9 or greater, about 8.0 or greater, about 8.1 or greater, about 8.2 or greater, about 8.3 or greater, about 8.4 or greater, about 8.5 or greater, about 8.6 or greater, about 8.7 or greater, about 8.8 or greater, about 8.9 or greater, or about 9.0 or greater. In one embodiment, the pH may be about 7.9 or greater.

In some embodiments, the FXN protein may be combined with a reducing agent and an ROS detector compound at a pH of about 7.4 to about 8.0, about 7.6 to about 8.3, about 7.7 to about 8.4, about 7.9 to about 8.7, about 8.0 to about 8.5, about 8.2 to about 8.7, about 8 to about 9, or about 8.5 to about 9.

In some embodiments, the present disclosure also provides compositions for measuring activity of an FXN protein that comprise an FXN protein, a reducing agent and a reactive oxygen species (ROS) detector compound, wherein pH of the composition is greater than about 7.4, e.g., greater than about 7.5, greater than about 7.6, greater than about 7.7, greater than about 7.8, greater than about 7.9, greater than about 8.0, greater than about 8.1, greater than about 8.2, greater than about 8.3, greater than about 8.4, greater than about 8.5, greater than about 8.6, greater than about 8.7, greater than about 8.8, greater than about 8.9, or greater than about 9.0. In one embodiment, the pH may be greater than about 7.9.

In some embodiments, the present disclosure provides compositions for measuring activity of an FXN protein that comprise an FXN protein, a reducing agent and a reactive oxygen species (ROS) detector compound, wherein pH of the composition is about 7.4 or greater, e.g., about 7.5 or greater, about 7.6 or greater, about 7.7 or greater, about 7.8 or greater, about 7.9 or greater, about 8.0 or greater, about 8.1 or greater, about 8.2 or greater, about 8.3 or greater, about 8.4 or greater, about 8.5 or greater, about 8.6 or greater, about 8.7 or greater, about 8.8 or greater, about 8.9 or greater, or about 9.0 or greater. In one embodiment, the pH may be about 7.9 or greater.

In some embodiments, the present disclosure provides compositions for measuring activity of an FXN protein that comprise an FXN protein, a reducing agent and a reactive oxygen species (ROS) detector compound, wherein pH of the composition is about 7.4 to about 8.0, about 7.6 to about 8.3, about 7.7 to about 8.4, about 7.9 to about 8.7, about 8.0 to about 8.5, about 8.2 to about 8.7, about 8 to about 9, or about 8.5 to about 9.

In some embodiments, methods for measuring activity of an FXN protein provided by the present disclosure comprise combining the FXN protein with a reducing agent and a reactive oxygen species (ROS) detector compound, thereby producing an assay mixture. In this mixture, the FXN protein facilitates oxidation of the reducing agent and generation of ROS. The methods may further comprise incubating the assay mixture for a period of time to allow generation of ROS. The methods may further comprise measuring the amount of ROS generated after the incubation, e.g., by detecting a signal generated by an ROS detector compound.

In some examples, methods for measuring activity of a Frataxin (FXN) protein provided by the present disclosure comprise adding a metal ion into the assay mixture. The metal ion may be selected from the group consisting of $Mn^{2+}$, $Fe^{3+}$, $Zn^{2+}$, $Cu^{2+}$ and $Mg^{2+}$. In one specific example, the metal ion may be $Fe^{3+}$. In another specific example, the metal ion may be $Mn^{2+}$. In some embodiments, methods of the present disclosure may comprise adding more than one metal ion into the assay mixture. In one example, both $Fe^{3+}$ and $Mn^{2+}$ may both be added into the assay mixture in accordance with an embodiment of the disclosure.

In some examples, an FXN protein may exhibit a specific activity of hydroquinone reduction within the range of about 1000 mU/mg of FXN protein to about 6500 mU/mg of FXN protein. In an embodiment, an FXN protein may exhibit a specific activity of hydroquinone reduction within the range of about 1200 mU/mg to about 6000 mU/mg, about 1400 mU/mg to about 5900 mU/mg. MilliUnits (mU) of an FXN protein are as defined as the amount of an FXN protein that is necessary to achieve an initial assay velocity $V_i$=1.

Frataxin (FXN) Proteins

The present disclosure provides methods for measuring activity of a frataxin (FXN) protein. The term "frataxin protein" or "FXN protein", as used herein, refers to any polypeptide comprising frataxin (FXN), or a functional analogue, derivative or a fragment of FXN. FXN is an essential and phylogenetically conserved protein that is found in cells throughout the body, with the highest levels in the heart, spinal cord, liver, pancreas, and skeletal muscle. FXN is encoded in the nucleus, expressed in the cytoplasm and imported into the mitochondria where it is processed to the mature form.

In the context of the present disclosure, the FXN comprised in an "FXN protein" may be derived from any species, e.g., a mammalian species, such as a mouse, a cynomolgus macaque or a human. In one aspect, the FXN protein comprises human FXN (hFXN). In humans, hFXN is a 210-amino acid full-length hFXN (hFXN$_{1-210}$, 23.1 kDa) containing a typical mitochondrial targeting sequence (MTS) at the amino terminus that is processed in a 2-step cleavage by the mitochondrial matrix processing peptidase (MPP) as it is imported into the mitochondrial matrix. The resulting protein is a 130-amino acid, 14.2 kDa mature hFXN protein (hFXN$_{81-210}$). Sequences of the full-length hFXN and mature hFXN are shown in Table 1 below.

TABLE 1

Sequences of the full-length hFXN and mature hFXN.

| SEQ ID NO. | Protein | Amino Acid Sequence |
|---|---|---|
| 1 | Full-length hFXN hFXN$_{1-210}$ | MWTLGRRAVAGLLASPSPAQAQTLTRVPR PAELAPLCGRRGLRTDIDATCTPRRASSN QRGLNQIWNVKKQSVYLMNLRKSGTLGHP GSLDETTYERLAEETLDSLAEFFEDLADK PYTFEDYDVSFGSGVLTVKLGGDLGTYVI NKQTPNKQIWLSSPSSGPKRYDWTGKNWV YSHDGVSLHELLAAELTKALKTKLDLSSL AYSGKDA |
| 2 | Mature hFXN hFXN$_{81-210}$ | SGTLGHPGSLDETTYERLAEETLDSLAEF FEDLADKPYTFEDYDVSFGSGVLTVKLGG DLGTYVINKQTPNKQIWLSSPSSGPKRYD WTGKNWVYSHDGVSLHELLAAELTKALKT KLDLSSLAYSGKDA |

The full-length hFXN (SEQ ID NO: 1) comprises mature hFXN (SEQ ID NO: 2) and a mitochondrial targeting sequence (MTS) having the amino acid sequence (SEQ ID NO: 3)
MWTLGRRAVAGLLASPSPAQAQTLTRVPRPAELAPLCGRRGLRTDIDATC

TPRRASSNQRGLNQIWNVKKQSVYLMNLRK.

In some examples, the FXN protein comprises hFXN, e.g., full-length hFXN (SEQ ID NO: 1) or mature hFXN (SEQ ID NO: 2). In some examples, the FXN protein comprises a functional fragment of hFXN. In some examples, the FXN protein comprises a derivative of hFXN. In some examples, the FXN protein comprises a functional analog of hFXN.

In some examples, the FXN protein may be an FXN fusion protein. As used herein, the term "FXN fusion protein" refers to an artificial polypeptide that comprises FXN, e.g., full-length hFXN (SEQ ID NO: 1) or mature hFXN (SEQ ID NO: 2), or a functional analogue, derivative or a fragment of FXN, and an additional moiety. The additional moiety that may be comprised in an FXN fusion protein may be a protein different from FXN, e.g., a full-length protein or a fragment of a protein. In some examples, the FXN fusion protein may comprise FXN, e.g., full-length hFXN (SEQ ID NO: 1) or a mature hFXN (SEQ ID NO: 2), and a cell penetrating peptide (CPP) as an additional moiety.

The term "cell penetrating peptide" or "CPP", as used herein, refers to a short peptide sequence, typically between 5 and 30 amino acids long, that can facilitate cellular intake of various molecular cargo, such as proteins. Within the context of the present disclosure, a CPP present in an FXN fusion protein facilitates the delivery of the FXN fusion protein into a cell, e.g., a recipient cell. Once inside the cell, the FXN fusion protein may be processed by cellular machinery to remove the CPP the FXN fusion protein.

CPPs may be polycationic, i.e., have an amino acid composition that either contains a high relative abundance of positively charged amino acids, such as lysine or arginine. CCPs may also be amphipathic, i.e., have sequences that contain an alternating pattern of polar/charged amino acids and non-polar, hydrophobic amino acids. CPPs may also be hydrophobic, i.e., contain only apolar residues with low net charge, or have hydrophobic amino acid groups that are crucial for cellular uptake.

A CPP that may be comprised in the FXN fusion protein useful in the context of the present invention may be any CPP known to a person skilled in the art. For example, the CPP may be any CPP listed in the Database of Cell-Penetrating Peptides CPPsite 2.0, the entire contents of which are hereby incorporated herein by reference. For examples, CPPs useful in the context of the present invention may be a cell penetrating peptide derived from a protein selected from the group consisting of HIV Trans-Activator of Transcription peptide (HIV-TAT), galanin, mastoparan, transportan, penetratin, polyarginine, or VP22. In some embodiments, the CPP may comprise a TAT protein domain comprising amino acids 47-57 of the 86 amino acid full length HIV-TAT protein (which 11 amino acid peptide may also be referred to herein as "HIV-TAT"; SEQ ID NO: 4). In one embodiment, the CPP consists of HIV-TAT (SEQ ID NO: 4). In some embodiments, the CPP comprises amino acids 47-57 of the 86 amino acid full length HIV-TAT protein with a methionine added at the amino terminus for initiation (12 AA; "HIV-TAT+M"): MYGRKKRRQRRR (SEQ ID NO: 5). Table 2 below lists amino acid sequences of exemplary CPPs.

TABLE 2

Exemplary CPPs and corresponding sequences

| SEQ ID NO. | CPP | Amino Acid Sequence |
|---|---|---|
| 4 | HIV-TAT | YGRKKRRQRRR |
| 5 | HIV-TAT + M | MYGRKKRRQRRR |
| 6 | Galanin | GWTLNSAGYLLGPHAVGNHRSFSDKNGLTS |
| 7 | Mastoparan | INLKALAALAKKIL-NH$_2$ |
| 8 | Transportan | GWTLNSAGYLLGKINLKALAALAKKIL |
| 9 | Penetratin | RQIKIWFQNRRMKWKK |
| 10 | Poly-arginine | RRRRRRRRR |
| 11 | VP22 | DAATATRGRSAASRPTERPRAPARSASRPRRPVE |

In some aspects, an FXN fusion protein may comprise full length hFXN, e.g., SEQ ID NO: 1, or an amino acid sequence having at least 85%, e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of the full length hFXN, e.g., SEQ ID NO: 1 as listed in Table 1.

In some aspects, an FXN fusion protein may comprise mature hFXN, e.g., SEQ ID NO: 2, or an amino acid sequence having at least 85%, e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of the mature hFXN, e.g., SEQ ID NO: 2 as listed in Table 1.

In some aspects, an FXN fusion protein may comprise an MTS, e.g., SEQ ID NO: 3, or an amino acid sequence having at least 85%, e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the sequence of the MTS, e.g., SEQ ID NO: 3.

In some aspects, an FXN fusion protein may comprise HIV-TAT as a CPP, e.g., SEQ ID NO: 4, or an amino acid sequence having at least 85%, e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the HIV-TAT, e.g., SEQ ID NO: 4. In some aspects, an FXN fusion protein may comprise HIV-TAT as a CPP with a methionine added at the amino terminus for initiation, e.g., SEQ ID NO: 5, or an amino acid sequence having at least 85%, e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 5.

In some examples, the CPP comprised in the FXN fusion protein is HIV-TAT (SEQ ID NO: 4). In some embodiments, the FXN fusion protein may comprise full-length FXN, e.g., SEQ ID NO: 1, and HIV-TAT, e.g., SEQ ID NO: 4, as CPP.

In some embodiments, the FXN fusion protein may comprise mature FXN, e.g., SEQ ID NO: 2, MTS, e.g., SEQ ID NO: 3 and HIV-TAT, e.g., SEQ ID NO: 4, as CPP.

In some embodiments, in FXN fusion proteins of the present disclosure, the CPP may be fused together with the FXN, e.g., full-length FXN, or fused together with MTS, via a linker to form a single polypeptide chain. In some embodiments, the linker may comprise the amino acid sequence GG.

In some embodiments, the FXN fusion protein comprises the following amino acid sequence (224 amino acids): MYGRKKRRQRRRGGMWTLGRRAVAGL-LASPSPAQAQTLTRVPRPAELAPLCGRRGLR TDI-DATCTPRRASSNQR-GLNQIWNVKKQSVYLMNLRKSGTLGHPGSLDETTY ERLAEET LDSLAEFFEDLADKPYT-FEDYDVSFGSGVLTVKLGGDLGTYVINKQTPNKQIW LSSPSSG PKRYDWTGKNWVYSHDGVSLHELLAAEL-TKALKTKLDLSSLAYSGKDA (SEQ ID NO: 12). In some embodiments, the FXN fusion protein consists of the amino acid sequence of SEQ ID NO: 12. The FXN fusion proteins comprising, or consisting of, SEQ ID NO: 12 is further described in U.S. Provisional Patent Application Nos. 62/891,029 and U.S. patent application Ser. No. 16/942,276, the entire contents of each of which are hereby incorporated herein by reference.

In some embodiments, methods of the present disclosure may be used for measuring activity of an FXN protein, e.g., an FXN fusion protein, which may comprise an FXN or a functional analog, derivative, or a fragment of FXN. The term "derivative", as used herein, encompasses amino acid sequences (polypeptides) which differ from the polypeptides specifically defined in the present disclosure, e.g., SEQ ID NOS. 1-3, by insertions, deletions, substitutions and modifications of amino acids that do not substantially alter the activity of the original polypeptide. It should be appreciated that by the terms "insertion(s)", "deletion(s)" or "substitution(s)", as used herein, encompasses any addition, deletion or replacement, respectively, of between 1 and 50 amino acid residues of a polypeptide, e.g., between 1 and 5 amino acid residues, between 1 and 10 amino acid residues, between 5 and 15 amino acid residues, between and 20 amino acid residues, between 25 and 40 amino acid residues or between 30 and 50 amino acid residues. More particularly, insertion(s), deletion(s) or substitution(s) may be of any one of 1, 2, 3, 4, 5, 6, 7, 8, 9, or 10 amino acid residues. It should be noted that the insertion(s), deletion(s) or substitution(s) may occur in any position of the modified peptide, as well as in any of the N' or C' termini thereof.

In some embodiments, the amino acid sequence of an FXN protein within the context of the present disclosure may differ from the amino acid sequence of a naturally occurring FXN, e.g., hFXN. For example, an FXN protein may include a conservative amino acid substitution, i.e., substitution with a structurally-similar amino acid. For instance, structurally similar amino acids include: (isoleucine (I), leucine (L) and valine (V)); (phenylalanine (F) and tyrosine (Y)); (lysine (K) and arginine (R)); (glutamine (Q) and asparagine (N)); (aspartic acid (D) and glutamic acid (E)); and (glycine (G) and alanine (A)).

The term "derivative", as used herein, encompasses homologues, variants and analogues of the original polypeptide, e.g., FXN, as well as covalent modifications of the original polypeptide. A derivative, a variant and an analogue of FXN will have substantially the same biological activity as its native form.

Reducing Agent

Methods provided by the present disclosure comprise combining an FXN protein with a reducing agent and an ROS detector compound, thereby producing an assay mixture. The term "reducing agent", as used herein, refers to any reducing agent that, when combined with an FXN protein, results in production of ROS, e.g., superoxide. In some examples, a reducing agent may be an organic compound. In further examples, the organic compound may be a reduced quinone compound.

The term "quinone compound", as used herein, refers to compounds having a fully conjugated cyclic dione structure derived from aromatic compounds by conversion of an even number of number of —CH= groups into —C(=O)— groups with any necessary rearrangement of double bonds (polycyclic and heterocyclic analogues are included). For example, a quinone compound may comprise an aromatic group comprising an even number of —C(=O)— groups. In some aspects, the aromatic group of a quinone compound may comprise a moiety having one or more, e.g., two, three, four, five or six or more conjugated rings. For example, the quinone compound may be a benzoquinone compound, i.e., a compound comprising a benzoquinone having a single aromatic ring. In another example, the quinone compound may be a naphthoquinone compound, i.e., a compound comprising a naphthoquinone having two conjugated aromatic rings. In yet another example, the quinone compound may be an anthraquinone compound, i.e., a compound comprising anthraquinone comprising three aromatic rings.

A quinone compound comprising —C(=O)— groups is in an oxidized form. In some embodiments, the quinone compound may be a reduced quinone compound, wherein the —C(=O)— groups have been reduced to —C—OH groups. Exemplary quinone compounds in their oxidized and reduced forms are shown in Table 3 below.

TABLE 3

Exemplary quinone compounds

| Name | Oxidized Form | Reduced Form |
| --- | --- | --- |
| Benzoquinone | 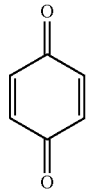 | 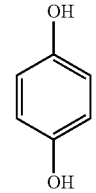 |
| Naphthoquinone | 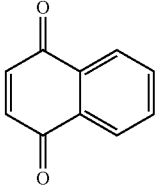 [SMILES: O=C1C=CC(=O)c2ccccc21] | 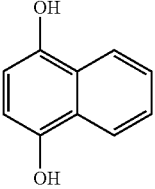 |

TABLE 3-continued

Exemplary quinone compounds

| Name | Oxidized Form | Reduced Form |
| --- | --- | --- |
| Anthraquinone | 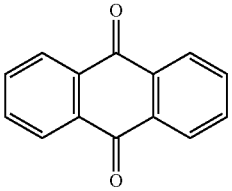 [SMILES: O=C1c2ccccc2C(=O)c2ccccc21] | 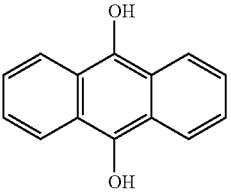 [SMILES: Oc1c2ccccc2c(O)c2ccccc12] |

In one example, the reducing agent useful in the methods of the present disclosure is a reduced quinone compound, e.g., a reduced benzoquinone compound, a reduced naphthoquinone compound or reduced anthraquinone compound. In a further example, the reducing agent is a reduced benzoquinone compound, such as hydroquinone having the following structure:

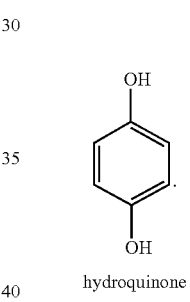

hydroquinone

ROS Detector Compound

Methods provided by the present disclosure comprise combining an FXN protein with a reducing agent and an ROS detector compound, thereby producing an assay mixture. The term "ROS detector compound", as used herein, refers to any compound that is capable of producing a detectable signal in response to ROS, e.g., superoxide, which is generated in the presence of an FXN protein and a reducing agent. In some examples, the ROS detector compound may be a fluorescent probe or a chemiluminescent probe. In some examples, the ROS detector compound may be a superoxide detection reagent, i.e., a reagent that is capable of producing a signal in response to superoxide, or a hydrogen peroxide detection reagent, i.e., a reagent that is capable of producing a signal in response to hydrogen peroxide. Exemplary ROS detector compounds, e.g., a superoxide detection reagent or a hydrogen peroxide detection reagent, may be found, for example, in a ThermoFisher Scientific catalog. In some embodiments, the superoxide anion detection reagents may be selected from the reagents shown in Table 4 below and structural analogs or variants thereof.

TABLE 4
Exemplary ROS detector compounds
| Name | Structure |
|---|---|
| coelenterazine | 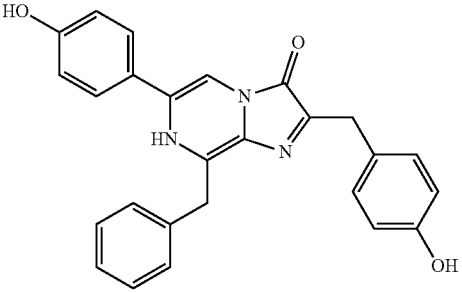 [SMILES: O=c1c(Cc2ccc(O)cc2)nc2c(Cc3ccccc3)[nH]c(-c3ccc(O)cc3)cn1-2] |
| dihydroethidium | 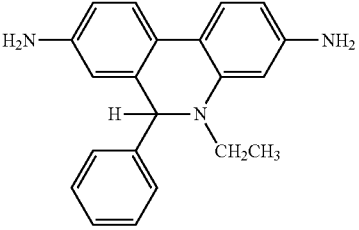 [SMILES: CCN1c2cc(N)ccc2-c2ccc(N)cc2C1c1ccccc1] |
| 2',7'-dichlorodihydrofluorescein diacetate (H$_2$DCFDA) | 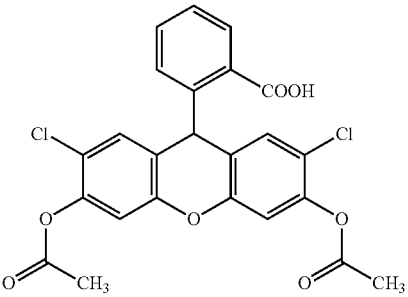 [SMILES: CC(=O)Oc1cc2c(cc1Cl)C(c1ccccc1C(=O)O)c1cc(Cl)c(OC(C)=O)cc1O2] |
| 2',7'-dichlorodihydrofluorescein (H$_2$DCF) | 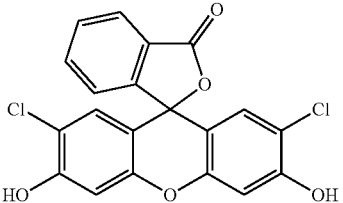 [SMILES: O=C1OC2(c3cc(Cl)c(O)cc3Oc3cc(O)c(Cl)cc32)c2ccccc21] |
| lucigenin | 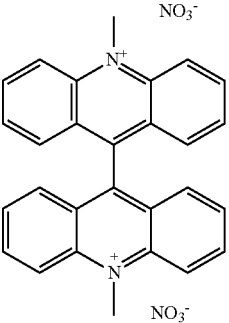 |

TABLE 4-continued

Exemplary ROS detector compounds

| Name | Structure |
|---|---|
| luminol | 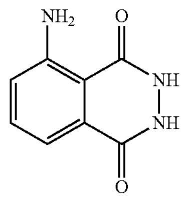 [SMILES: Nc1cccc2c(=O)[nH][nH]c(=O)c12] |
| Cypridina Luciferin Analog (CLA) | 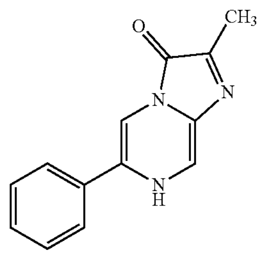 [SMILES: Cc1nc2c[nH]c(-c3ccccc3)cn-2c1=O] |
| Cypridina Luciferin methoxy-analogue (MCLA) | 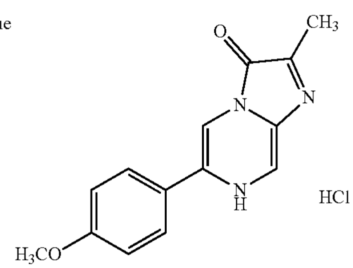 |
| Methylthiazolyldiphenyl-tetrazolium bromide (MTT) | 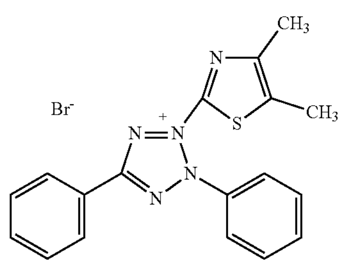 |
| p-Nitrotetrazolium blue (NBT) | 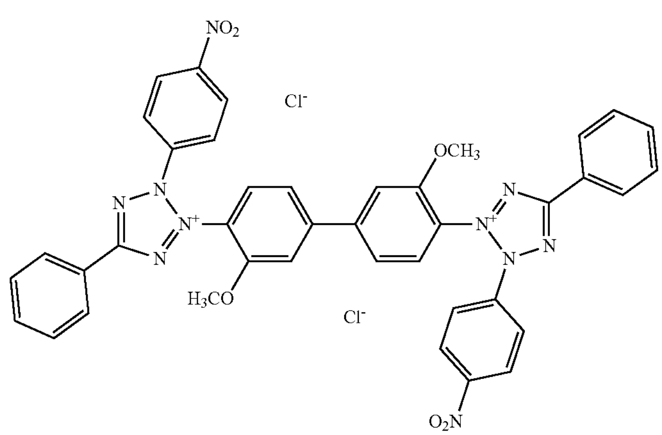 [SMILES: COc1cc(-c2ccc(-[n+]3nc(-c4ccccc4)nn3-c3ccc([N+](=O)[O-])cc3)c(OC)c2)ccc1-[n+]1nc(-c2ccccc2)nn1-c1ccc([N+](=O)[O-])cc1 ; [Cl-] ; [Cl-]] |

TABLE 4-continued

Exemplary ROS detector compounds

| Name | Structure |
|---|---|
| RedoxSensor Red CC-1 | 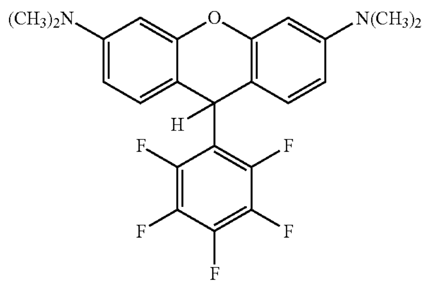 |
| 2,3-Bis-(2-Methoxy-4-Nitro-5-Sulfophenyl)-2H-Tetrazolium-5-Carboxanilide (XTT) | 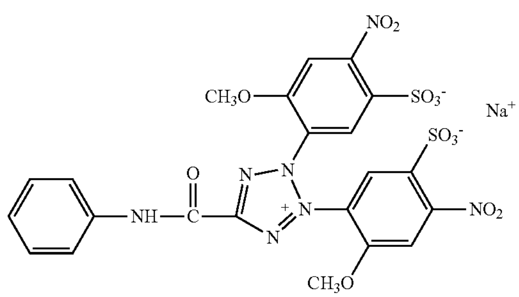 |

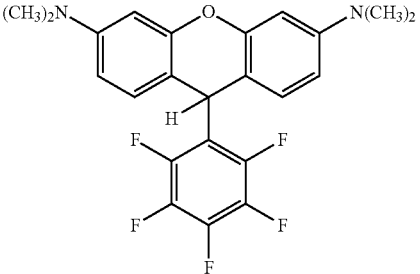

In a specific embodiment, the ROS detector compound is 2',7'-dichlorodihydrofluorescein ($H_2DCF$). $H_2DCF$ may be obtained from the commercially available 2',7'-dichlorodihydrofluorescein diacetate ($H_2DCFDA$) by treating it, e.g., with a base, to remove acetyl groups (see, e.g., Example 1 of the present disclosure). In the presence of ROS, $H_2DCF$ is oxidized to 2'-7'-dichlorofluorescein (DCF), which is highly fluorescent and may be used for the quantitation of ROS. The reported wavelengths for the measurement of DCF fluorescence are 498 nm for excitation and 522 nm for emission.

In some examples, the ROS detector compound may be an anti-oxidant compound or an ROS scavenger compounds. An ROS detector compound may also be a hydrogen peroxide probe. For example, certain fluorogenic substrates produce intensely fluorescent products in the presence of hydrogen peroxide ($H_2O_2$) and horseradish peroxidase (HRP) enzyme, which may be measured. Such fluorogenic substrates may also be used in the methods of the present disclosure to measure the amount of ROS generated as a result of an FXN protein activity.

In one embodiment, an ROS detector compound may be a hydrogen peroxide probe, such as Peroxy Green 1 (PG1) of the structure 9-(4-methoxy-2-methylphenyl)-6-(4,4,5,5-tetramethyl-1,3,2-dioxaborolan-2-yl)-3H-xanthen-3-one, as shown below:

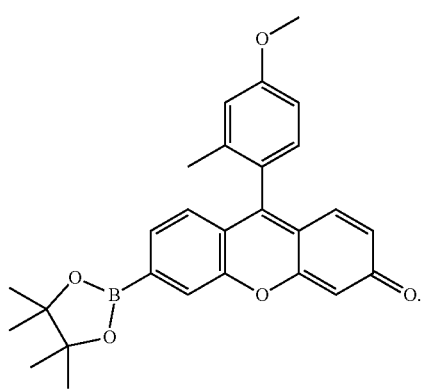

Peroxy Green 1 (PG1)

In another embodiment, an ROS detector compound may be a hydrogen peroxide probe, such as Peroxy Crimson 1 (PC1) of the structure 7-(4,4,5,5-Tetramethyl-1,3,2-dioxaborolan-2-yl)-3H-phenoxazin-3-one, as shown below:

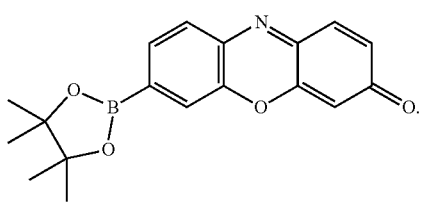

Peroxy Crimson 1 (PC1)

PG1 and PC1 are boronate-based hydrogen peroxide probes that have visible-wavelength excitation and emission wavelengths. A reaction with hydrogen peroxide results in a 10-fold and 40-fold increase in the fluorescence of PG1 and PC1, respectively. PG1 features an excitation wavelength of 460 nm with emission maxima at 510 nm, while PC1 demonstrates improved characteristics of red-shifted excitation and larger stokes shift which reduces autofluorescence (excitation: 480 nm; emission: 584 nm).

In some example, the ROS detector compound may be a hydrogen peroxide probe, such as homovannilic acid, having a structure as shown below:

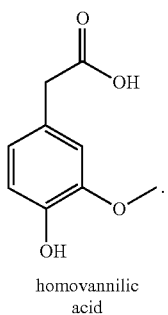

homovannilic acid

Homovannilic acid dimerizes when oxidized by hydrogen peroxide through horseradish peroxidase catalysis. As a monomer, homovannilic acid is non-fluorescent, but as a dimer, homovannilic acid possesses a peak excitation wavelength of 315 nm, with an emission wavelength of 425 nm.

In some examples, an ROS detector compound may be a protein, e.g., an engineered protein, that comprises a redox-reactive domain capable of inducing a conformational change in the protein upon reacting with ROS. For example, a fluorescent protein may be engineered to comprise a redox-reactive domain and to change conformation upon redox activity of the redox-reactive domain. One such exemplary protein, called HyPer, consists of a circularly permuted yellow fluorescent protein (cpYFP) inserted into the regulatory domain of the prokaryotic $H_2O_2$-sensing protein, OxyR.

In some examples, an ROS detector compound may comprise a label, wherein the label may be an integral part of the ROS detector compound, as for example in DCF. Alternatively, the label may be covalently linked to the ROS detector compound.

By way of example, a label comprised in an ROS detector compound may be a fluorescent label, a colorimetric label, or luminescence-based label. Fluorescence may be measured with a standard fluorometer; luminescence may be measured with a standard luminometer, and colorimetric labels may be measured with a standard colorimeter.

In some examples, a reducing agent and an ROS detector compound may be the same compound. Such compound may be capable of being oxidized by an FXN protein and generating ROS, e.g., superoxide, while simultaneously emitting a detectable signal in its oxidized form. One such exemplary compound is $H_2DCF$.

In other examples, a reducing agent and an ROS detector compound may be different compounds. For example, a reducing agent may be a reduced quinone compound, e.g., hydroquinone, and the ROS detector compound may be $H_2DCF$.

In the description, unless otherwise stated, adjectives such as "substantially" and "about" modifying a condition or relationship characteristic of a feature or features of an embodiment of the disclosure, are understood to mean that the condition or characteristic is defined to within tolerances that are acceptable for operation of the embodiment for an application for which it is intended. Unless otherwise indicated, the word "or" in the description and claims is considered to be the inclusive "or" (having the meaning of and/or) rather than the exclusive or, and indicates at least one of, or any combination of items it conjoins.

In the description and claims of the present application, each of the verbs, "comprise" "include" and "have", and conjugates thereof, are used to indicate that the object or objects of the verb are not necessarily a complete listing of components, elements or parts of the subject or subjects of the verb.

Kits for Measuring Activity of an FXN Protein

The present disclosure also provides kits for use in determining activity of an FXN protein. Such kits may comprise a reducing agent, an ROS detector compound and instructions for use. For example, the instructions for use may comprise instructions to combine the reducing agent, the ROS detector compound and an FXN protein, thereby producing an assay mixture. The instructions for use may further comprise instructions for determining Vi of the FXN protein in the assay mixture.

The kits provided by the present disclosure may be used to determine activity of any FXN protein as described herein. In one embodiment, the FXN protein may be a human FXN protein, e.g., comprising SEQ ID NO: 1 or SEQ ID NO: 2. In one embodiment, the FXN protein may be an FXN fusion protein, e.g., comprising or consisting of SEQ ID NO: 12.

In some embodiments, the kit may further comprise a metal ion compound, e.g., a salt. The term "metal ion compound" as used herein, refers to a compound that, when dissolved in an aqueous solution, may be a source of metal ions. In some embodiments, the metal ions may be selected from the group consisting of $Mn^{2+}$, $Fe^{3+}$, $Zn^{2+}$, $Cu^{2+}$ and $Mg^{2+}$. In one embodiment, the metal ion is $Fe^{3+}$. In another embodiment, the metal ion is $Mn^{2+}$. In another embodiment, the metal ion is $Zn^{2+}$. In another embodiment, the metal ion is $Cu^{2+}$. In another embodiment, the metal ion is $Mg^{2+}$. In one embodiment, the metal ion compound may be $MgCl_2$.

In some embodiments, the reducing agent may be as described herein. In one embodiment, the reducing agent is hydroquinone.

In some embodiments, the ROS detector compound may be as described herein. In one embodiment, the ROS detector compound is 2',7'-dichlorodihydrofluorescein ($H_2DCF$).

Methods for Identifying Compounds Capable of Modulating FXN Activity

The present disclosure also provides methods for identifying a compound capable of modulating activity of an FXN protein. The methods comprise measuring the activity of the FXN protein in accordance with methods of the present disclosure in the presence of a test compound, thereby identifying a compound capable of modulating activity of an FXN protein.

In some embodiments, the present disclosure provides a method for identifying a compound capable of modulating activity of a Frataxin (FXN) protein that comprises combining the FXN protein with a test compound, a reducing agent and a reactive oxygen species (ROS) detector compound, thereby producing an assay mixture, wherein the FXN protein facilitates oxidation of the reducing agent and generation of ROS; and measuring the amount of ROS generated in the presence of the test compound. In some embodiments, the method further comprises determining Vi of the FXN protein. In some embodiments, the method further comprises comparing the Vi of the FXN protein in the presence of the test compound with Vi of the FXN protein in the absence of the test compound and identifying the test compound as a compound capable of modulating activity of the FXN protein when Vi of the FXN protein in the presence of the test compound is different from Vi of the FXN protein in the absence of the test compound.

In some embodiments, the method further comprises comparing the Vi of the FXN protein in the presence of the test compound with Vi of the FXN protein in the absence of the test compound and identifying the test compound as a compound capable of increasing activity of the FXN protein when Vi of the FXN protein in the presence of the test compound is greater than the Vi of the FXN protein in the absence of the test compound.

In some embodiments, the method further comprises comparing the Vi of the FXN protein in the presence of the test compound with Vi of the FXN protein in the absence of the test compound and identifying the test compound as a compound capable of decreasing activity of the FXN protein when Vi of the FXN protein in the presence of the test compound is lower than the Vi of the FXN protein in the absence of the test compound.

In some embodiments, the method further comprises adjusting pH of the assay mixture to a pH of greater than about 7.4, or about 7.4 or greater. In some embodiment, the method comprises adjusting pH of the assay mixture to a pH of greater than about 7.9, or pH of about 7.9 or greater. In one embodiment, the method comprises adjusting pH of the assay mixture to about 8.0. In one embodiment, the method comprises adjusting pH of the assay mixture to a pH of about 7.4 to about 8.0, about 7.6 to about 8.3, about 7.7 to about 8.4, about 7.9 to about 8.7, about 8.0 to about 8.5, about 8.2 to about 8.7, about 8 to about 9, or about 8.5 to about 9.

In some embodiments, the method further comprises adding a metal ion to the assay mixture, e.g., a metal ion selected from the group consisting of $Mn^{2+}$, $Fe^{3+}$, $Zn^{2+}$, $Cu^{2+}$ and $Mg^{2+}$.

In one embodiment, the metal ion is $Mn^{2+}$. In another embodiment, the metal ion is $Fe^{3+}$. In another embodiment, the metal ion is $Zn^{2+}$. In another embodiment, the metal ion is $Cu^{2+}$. In another embodiment, the metal ion is $Mg^{2+}$.

In some embodiments, the reducing agent may be as described herein. In one embodiment, the reducing agent is hydroquinone.

In some embodiments, the ROS detector compound may be as described herein. In one embodiment, the ROS detector compound is 2',7'-dichlorodihydrofluorescein ($H_2DCF$).

The FXN protein may be any FXN protein as described herein. In one embodiment, the FXN protein may be a human FXN protein, e.g., comprising SEQ ID NO: 1 or SEQ ID NO: 2.

In one embodiment, the FXN protein may be an FXN fusion protein, e.g., comprising or consisting of SEQ ID NO: 12.

The term "compound capable of modulating activity of a Frataxin (FXN) protein", as used herein, refers to a compound that is capable of causing increased or decreased activity of the FXN protein, as measured by the methods of the present disclosure. In one embodiment, a compound capable of modulating activity of an FXN protein is capable of causing increased activity of the FXN protein. In another embodiment, a compound capable of modulating activity of an FXN protein is capable of causing decreased activity of the FXN protein.

An exemplary procedure that may be used to identify a compound capable of modulating activity of an FXN protein may comprise, e.g., a High Throughput Screening (HTS) of a compound library as described herein in Example 8.

The term "about", as used herein, can allow for a degree of variability in a value or range, such as a pH value, such that the value or range may be for example, within 10%, within 5%, within 1% or within 0.1% of a stated value or of a stated limit of a range.

Descriptions of embodiments of the disclosure in the present application are provided by way of example and are not intended to limit the scope of the disclosure. The described embodiments comprise different features, not all of which are required in all embodiments. Some embodiments utilize only some of the features or possible combinations of the features. Variations of embodiments of the disclosure that are described, and embodiments comprising different combinations of features noted in the described embodiments, will occur to persons of the art.

EXAMPLES

Example 1. Protocol for Hydroquinone (HQ) Reduction Assay

1. Activation of $H_2DCFDA$ to $H_2DCF$
   a. 1 ml of 1 mM $H_2DCFDA$ (in DMSO) is added to 20 mL of 0.01 M NaOH working solution to generate the activating solution. The solution is stirred for 30 minutes at room temperature in the dark.
   b. 79 mL of 33 mM $NaH_2PO_4$ solution is added to the activating solution to yield a final concentration of 10 μM $H_2DCF$.
   c. Activated $H_2DCFDA$ may be stored as 10 mL aliquots in the dark at 4° C. for up to 2 weeks.
2. Fluorescence Reading
   a. A multi-well plate containing the reaction mixture described in sections 3 to 5 below is shaken in a linear shaker at a frequency of 731 cpm (2 mm) for three (3) seconds before every read.
   b. Excitation and emission reading of the plate is performed every minute, or as required, with a spectrometer set for the following parameters: excitation at 485/20, emission at 528/20, optics from the top, a read height of 1 mm, and a gain of 50.
3. HQ Assay Plate Preparation
   a. Polystyrene 96-well plates (black, flat bottom with a non-binding surface) are recommended to be used for the assay. Equivalent alternatives may also be used.
   To each well add:
   i. 10 μL of 20× Hydroquinone (to 20 μM final concentration)
   ii. 10 μL of 20×$Mn^2$ (5 μM final concentration)

b. Tris Buffer Addition
  i. FXN protein sample well: 168 μL
  ii. DCF Standard Curve well: 170 μL
An example of a HQ assay plate is detailed below in Table 5.

TABLE 5

Assay plate for HQ assay

| Assay Plate | Control FXN Protein | Test FXN Protein Batch | DCF Standard Curve |
|---|---|---|---|
| A | 3 μM | 3 μM | 1 μM |
| B | 1 μM | 1 μM | 0.5 μM |
| C | 0.3 μM | 0.3 μM | 0.25 μM |
| D | 0.1 μM | 0.1 μM | 0.125 μM |
| E | 0.03 uM μM | 0.03 μM | 0.0625 μM |
| F | 0.01 μM | 0.01 μM | 0.0313 μM |
| G | 0 (Blank) Control | 0 (Blank) Control | 0.0156 μM |
| H | 0 (Blank) Control | 0 (Blank) Control | 0 μM (Blank) |

4. DCF Standard Dilution Plate
  a. 96-well plates (natural, 0.5 mL, V-bottom, sterile, single packed) are used as dilution plates.
  b. Preparation of 20×DCF standard curve
    i. 500 μL of 20 μM DCF solution is diluted according to a plate map exemplified in Table 6 below.

TABLE 6

Compound (DCF) dilution plate

| Dilution Plate | 3 (DCF Standard Curve) |
|---|---|
| A | 500 μL DCF Working solution = [20 μM] |
| B | 200 μL H$_2$O + 200 μL Transfer from A3 = [10 μM] |
| C | 200 μL H$_2$O + 200 μL Transfer from B3 = [5 μM] |
| D | 200 μL H$_2$O + 200 μL Transfer from C3 = [2.5 μM] |
| E | 200 μL H$_2$O + 200 μL Transfer from D3 = [1.25 μM] |
| F | 200 μL H$_2$O + 200 μL Transfer from E3 = [0.0625 μM] |
| G | 200 μL H$_2$O + 200 μL Transfer from F3 = [0.3125 μM] |
| H | 200 μL H$_2$O = [0 μM] | c. Preparation of control and test FXN protein samples
  i. A 100×FXN protein serial dilution is done according to the plate map exemplified in Table 7 below.

TABLE 7

FXN protein dilution plate

| Dilution Plate | 1 (Control) | 2 (Test) |
|---|---|---|
| A | X μL of FXN protein + X μL Tris = 300 μM | X μL of test FXN protein + X μL Tris = [300 μM] |
| B | 6 μL A1 + 12 μL Tris = [100 μM] | 6 μL A2 + 12 μL Tris = [100 μM] |
| C | 1.5 μL A1 + 13.5 μL Tris = [30 μM] | 1.5 μL A2 + 13.5 μL Tris = [30 μM] |
| D | 1.5 μL B1 + 13.5 μL Tris = [10 μM] | 1.5 μL B2 + 13.5 μL Tris = [10 μM] |
| E | 1.5 μL C1 + 13.5 μL Tris = [3 μM] | 1.5 μL C2 + 13.5 μL Tris = [3 μM] |
| F | 1.5 μL D1 + 13.5 μL Tris = [1 μM] | 1.5 μL D2 + 13.5 μL Tris = [1 μM] |
| G | 20 μL Tris = [0 μM] | 20 μL Tris = [0 μM] |
| H | 20 μL Tris = [0 μM] | 20 μL Tris = [0 μM] |

5. Final HQ Assay Plate Preparation
  a. 10 μL from 20×DCF standard curve from the dilution plate (shown in Table 6) are transferred to the HQ assay plate according to the plate map as shown in Table 5.
  b. 10 μL of H$_2$DCF (10 μM working solution) is added to every well (except the DCF standard curve) to arrive at a final concentration of 0.5 μM H$_2$DCF.
  c. 2 μL of FXN protein from FXN protein dilution plate are promptly added (Table 6) to the HQ assay plate according to the plate map as shown in Table 5.
  d. Plates are quickly placed in the plate reader and the kinetic read must be started immediately.
  e. Steps (c) and (d) are time sensitive and are performed quickly.
6. Data Analysis
  a. Kinetic Analysis
    i. Comparison of multiple batches—Scatter Plot
      1. Each concentration of FXN protein is plotted on a separate graph.
      2. Arbitrary Fluorescence Units (AFU) will be on the Y-axis and Time [HH:MM or minutes] on the X-axis.
      3. Average of duplicate+/−standard deviation as the error bar.
  b. Maximum Initial Velocity (Vi) Analysis
    i. Maximum velocity kinetic analysis should be performed:
      1. From 2 to 20 minutes;
      2. Velocity calculated on 5 points;
      3. Relative fluorescence units (RFU) per minute.
    ii. $V_i$ generated from the fluorescence scanner is plotted on a scatter plot
      1. Background is subtracted from the control wells.
      2. Y axis represents Vi units.
      3. X axis represents concentration in [μM].
      4. Average of duplicate+/−standard deviation as the error bar.
  c. Milli-Unit Analysis
    i. Background is subtracted for the [0] DCF and the DCF standard curve plotted. The line should go through 0,0, and the slope recorded. The slope must be transformed from Y=mX→X=Y/m
    ii. Background is subtracted from the Vi using the [0 uM] control wells specified as rows G and H from Table 7
    iii. The values are divided by the slope and provide the Units (U).
    iv. Units are multiplied by 1,000 to milliUnits (mU).
    v. The chart presented in Table 8 is used to determine the mg of protein. mU divided by mg of protein results in mU/mg.

TABLE 8

Conversion of μM of FXN protein to mg per well

| Concentration of FXN protein in μM | mg per well of FXN Protein (25 kDa) |
|---|---|
| 3 | 0.015 |
| 1 | 0.005 |
| 0.3 | 0.0015 |
| 0.1 | 0.0005 |
| 0.03 | 0.00015 |
| 0.01 | 0.00005 | vi. Duplicates are averaged, and the standard deviation is recorded as the error.
  vii. The FXN protein μM concentration that appears to be the most linear in the $V_i$ scatter plot should be selected.

viii. Different batches may be plotted in a bar graph for comparing activity.

Example 2. FXN Fusion Protein as a Catalyst of Hydroquinone Oxidation

FXN fusion protein having the amino acid sequence of SEQ ID NO: 12 comprises a cell penetrating peptide, HIV-TAT (SEQ ID NO: 4), and a full length hFXN (SEQ ID NO: 1), linked through a linker at the N-terminus of the hFXN. The therapeutic properties of this FXN fusion protein have been demonstrated in vitro and in vivo. In vitro, the genomic footprint of FXN-deficient cell lines before and after FXN fusion protein treatment has been characterized, and a significant difference in the expression of a set of genes identified (data not shown). In vivo, treatment of an FDRA mouse model with a FXN fusion protein demonstrated measurable improvement in the cardiomyopathic phenotype, for example in cardiac contractility and other symptoms (data not shown).

Because frataxin replacement therapy, i.e., administration of the FXN fusion protein, demonstrated biological activity in vitro and in vivo, and may be used as a therapeutic for the treatment of conditions related to FXN deficit, an activity assay was developed in order to enable the comparison of FXN protein activity in different batches of an FXN protein, such as the FXN fusion protein having the amino acid sequence of SEQ ID NO: 12. The assay exploits previously unidentified properties of an FXN protein as a redox agent.

The hydroquinone (HQ) reduction assay was performed using the FXN fusion protein of SEQ ID NO: 12 and the basic protocol described in Example 1. The reduction of HQ in the presence of an FXN protein may be represented by Scheme 1 below:

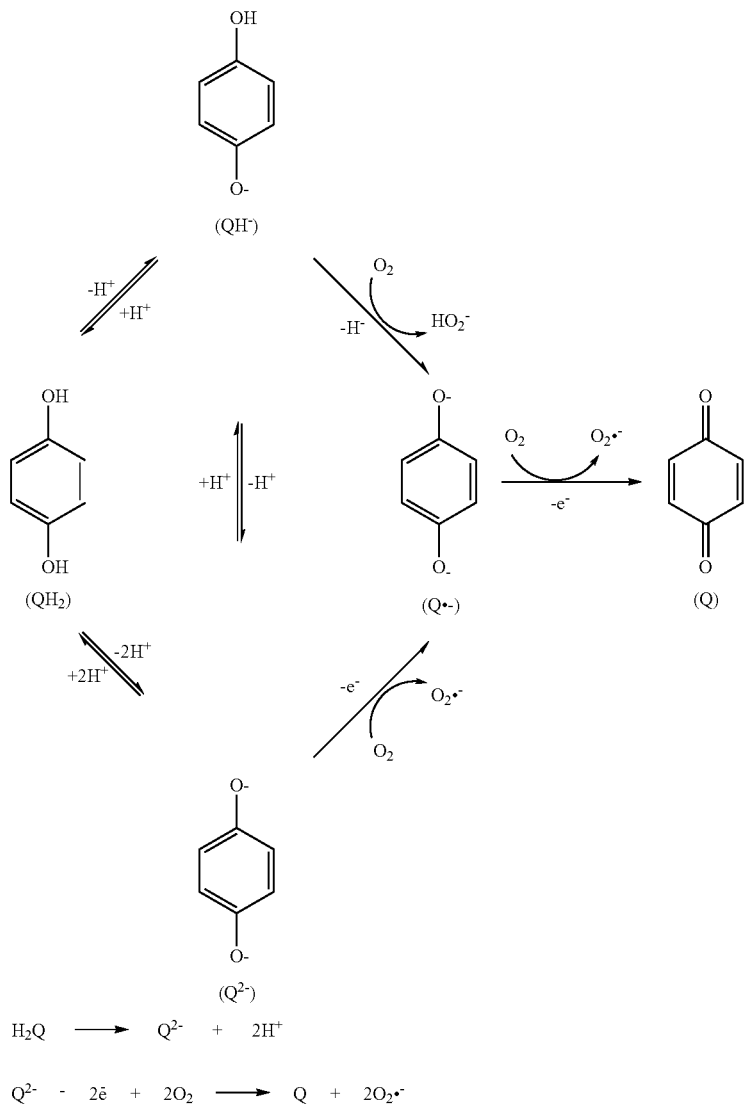

Figure 1B:
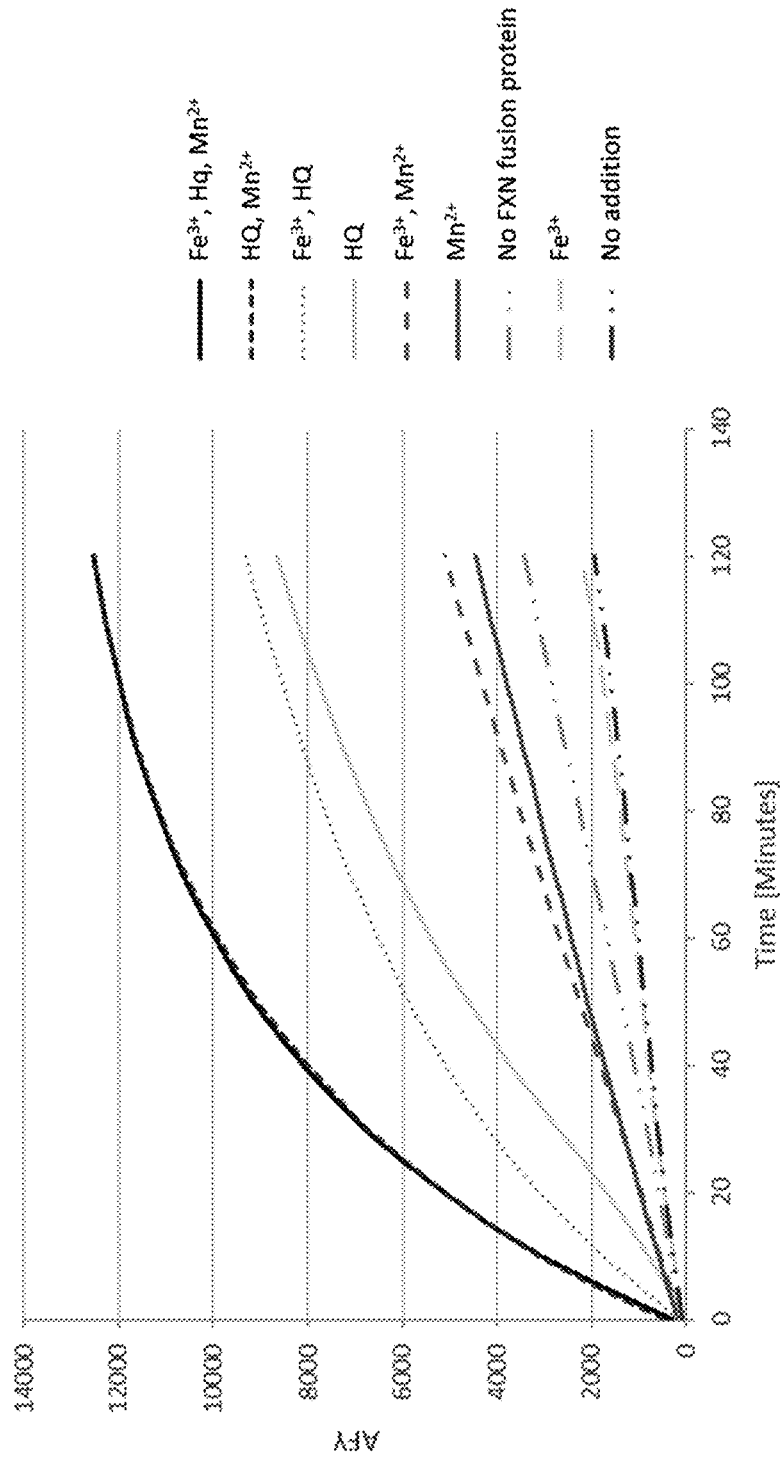
Figure 1C:
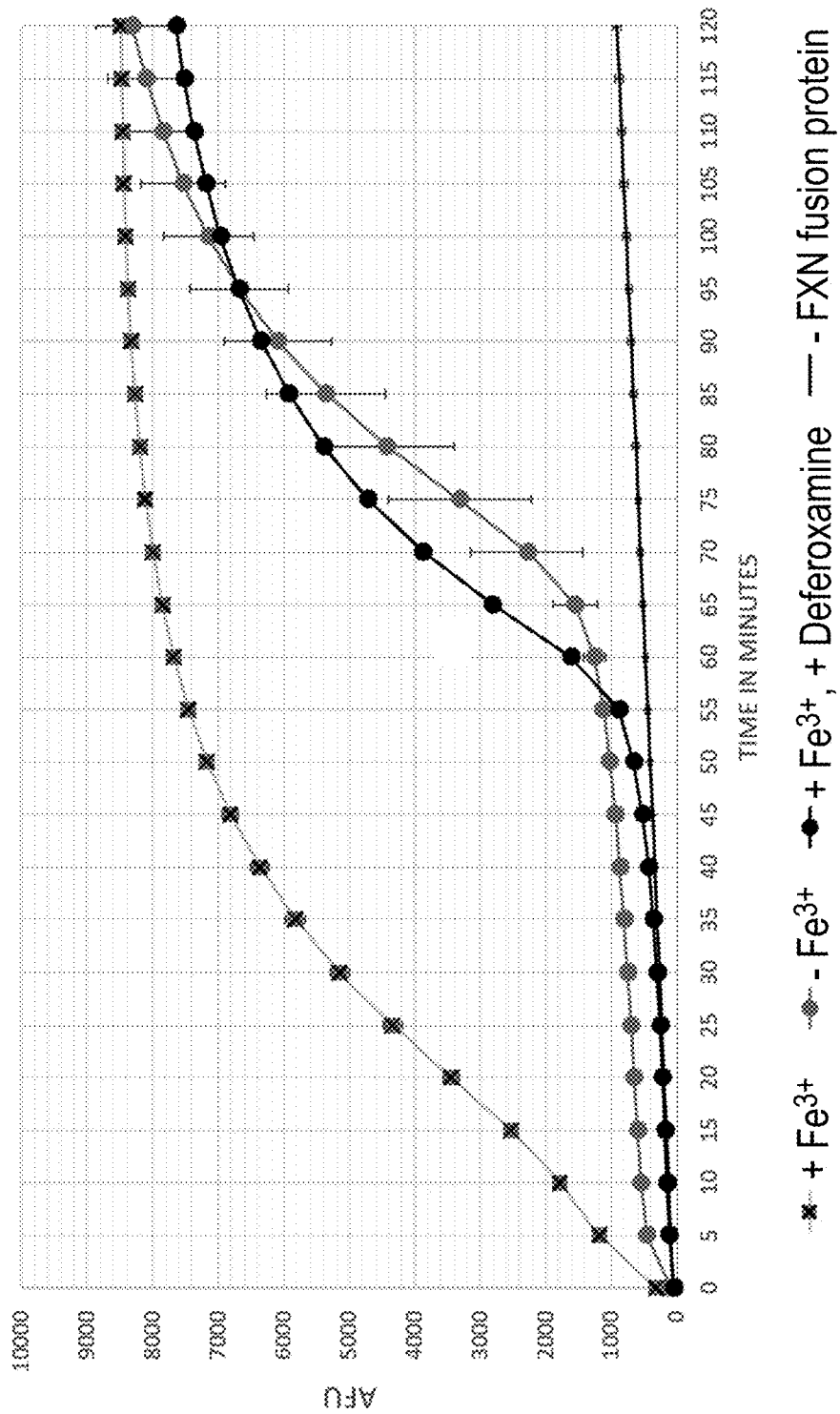

Generation of ROS, i.e., superoxide, was detected using an ROS detector compound, such as for example, 2',7'-dichlorodihydrofluorescein ($H_2DCF$), and was followed kinetically, as shown in Panel A of FIG. 1.

FIG. 1 shows the kinetics of hydroquinone (HQ) reduction in the presence of an exemplary FXN fusion protein, as measured by the amount of reactive oxygen species (ROS) generated over time. The amount of ROS is expressed as fluorescence, measured in arbitrary fluorescence units, AFU). Panel A of FIG. 1 is a graph showing the kinetics of superoxide ($O_2 \cdot^-$) generation via oxidation of hydroquinone (HQ) in the presence or absence of the exemplary FXN fusion protein.

The efficiency of the reaction was responsive to the presence of metal ions, in particular $Fe^{3+}$ and/or $Mn^{2+}$ ions. A comparison of the effect of the two metal ions was performed in an assay using 4.5 µM FXN fusion protein from two different batches. Table 9 provides the description of different samples, including the different combinations of reagents, tested in the experiment. In Table 9, a check mark (✓) indicates the presence of a given component in the assay mixture.

TABLE 9

Assay mixtures tested in the experiment

| Reaction No. | Corresponding Label in Panel B of FIG. 1 | Reaction Buffer | FXN Fusion Protein | HQ | $Fe^{3+}$ | $Mn^{2+}$ |
| --- | --- | --- | --- | --- | --- | --- |
| 1 | No addition | ✓ | | | | |
| 2 | No FXN fusion protein | ✓ | | ✓ | | |
| 3 | $Fe^{3+}$ | ✓ | ✓ | | ✓ | |
| 4 | $Mn^{2+}$ | ✓ | ✓ | | | ✓ |
| 5 | $Fe^{3+}$, $Mn^{2+}$ | ✓ | ✓ | | ✓ | ✓ |
| 6 | Hq | ✓ | ✓ | ✓ | | |
| 7 | $Fe^{3+}$, HQ | ✓ | ✓ | ✓ | ✓ | |
| 8 | Hq, $Mn^{2+}$ | ✓ | ✓ | ✓ | | ✓ |
| 9 | $Fe^{3+}$, Hq, $Mn^{2+}$ | ✓ | ✓ | ✓ | ✓ | ✓ |

Representative results of the experiment are provided in Panel B of FIG. 1. The results demonstrate that both $Mn^{2+}$ and $Fe^{3+}$ act as enhancers of FXN fusion protein, or co-factors, in the HQ oxidation reaction. Furthermore, in the presence of $Mn^{2+}$ alone, the speed of the reaction and fluorescence output are significantly higher than in the presence of $Fe^{3+}$ alone. Further, addition of $Fe^{3+}$ to the assay containing $Mn^{2+}$ did not have an have an incremental effect as compared to the assay containing $Mn^{2+}$ without $Fe^{3+}$.

In another experiment, the effect of the presence of $Fe^{3+}$ ions on the activity of an exemplary FXN fusion protein was studied. In this experiment, the kinetics of ROS generated over time was measured in assay mixtures containing 10 µM exemplary FXN fusion protein, 10 µM HQ, and 5 µM $H_2DCF$. One assay mixture also contained 1 mM deferoxamine, an iron chelator. FIG. 1, Panel C is a graph showing the kinetics of superoxide generation in the presence of an exemplary FXN fusion protein and $Fe^{3+}$ (gray squares); in the presence of an exemplary FXN fusion protein and in the absence of $Fe^{3+}$ (gray circles); in the presence of an exemplary FXN fusion protein, $Fe^{3+}$ and deferoxamine (black circles); and in the absence of an exemplary FXN fusion protein (small black rectangles).

The data shown in Panel C of FIG. 1 demonstrates that, under the conditions tested, ROS are generated both in the presence and in the absence of $Fe^{3+}$, however, in the absence of $Fe^{3+}$, a lag time of approximately 2 hours to ROS generation is observed.

The data shown in FIG. 1 demonstrates that an exemplary FXN fusion protein possesses enzymatic activity, as measured by ROS generation over time. This enzymatic activity is evident both in the presence and absence of metal ions, however, it is enhanced in the presence of metal ions, such as $Fe^{3+}$ and/or $Mn^{2+}$. Without being bound by a specific theory, it is believed that the presence of metal ions may induce a conformational change in an FXN protein, e.g., an FXN fusion protein, thereby enhancing its activity.

The FXN fusion protein activity assay described in this Example followed the basic protocol provided in Example 1, and the procedure is described below in more detail.

Protocol for Measuring Redox Activity of an Exemplary FXN Fusion Protein on Hydroquinone in the Presence of Metal Ions 1. Wells in columns 1-6 were loaded with:
   i. 10 µl of 100 µM HQ (5 µM final concentration);
   ii. 10 µl of 100 µM Fe(III) sulfate or 10 µl of 100 µM Mn(II) chloride (5 µM final concentration for both).
   Wells in columns 1-4 were further loaded with:
   iii. 160 µl of Tris-hydrochloride (THCl); and
   Wells in columns 5-6 were further loaded with:
   iv. 170 µl THCl.
2. Serial dilutions of an exemplary FXN fusion protein (SEQ ID NO. 12) for standard and test samples were prepared as described in Table 7, in which an initial 1:3 dilution (6 µL into 12 µL of 50 mM Tris-HCL, pH 8.0) was further diluted 1:10 (1.5 µL into 13.5 µL).
3. DCF serial dilution was prepared as described in Table 6, in which 10 µM DCF was diluted 1:1 (200 µL into 200 µL 0.04% DMSO in water).
4. 10 µL from the DCF standard curve plate (Table 6) was transferred to columns 5-6 of the 96-well HQ assay plate (Table 5).
5. 10 µL standard FXN protein or test FXN protein from the dilution plate as shown in Table 7 into columns 1-2 and columns 3-4 respectively of the 96-well HQ assay plate (Table 5).

As mentioned in the basic protocol described in Example 1 above, the following steps of adding 10 of activated $H_2DCF$ solution into each well in columns 1-4 (for a final $H_2DCF$ concentration of 0.5 µM), and transferring the plates to the plate reader for the kinetic read were performed very quickly.

An exemplary FXN fusion protein was incubated with HQ in the presence of Fe and/or $Mn^{2+}$, together with $H_2DCF$ as the ROS detector compound. Fluorescence was measured in a fluorescence plate reader, with an excitation filter at the range of 485 nm (485/20) and an emission filter at a range of 530 nm (528/20), optics from the top and gain of 50.

Titration of the commercially available oxidation product of DCF, 2',7'-dichlorofluorescein, enabled the establishment of assay conditions that showed the linearity between the amount of product in the reaction and the fluorescence readout. The titration provided the basis for the definition of "units of an exemplary FXN fusion protein" used for the different batches of the exemplary FXN fusion protein.

Figure 2:
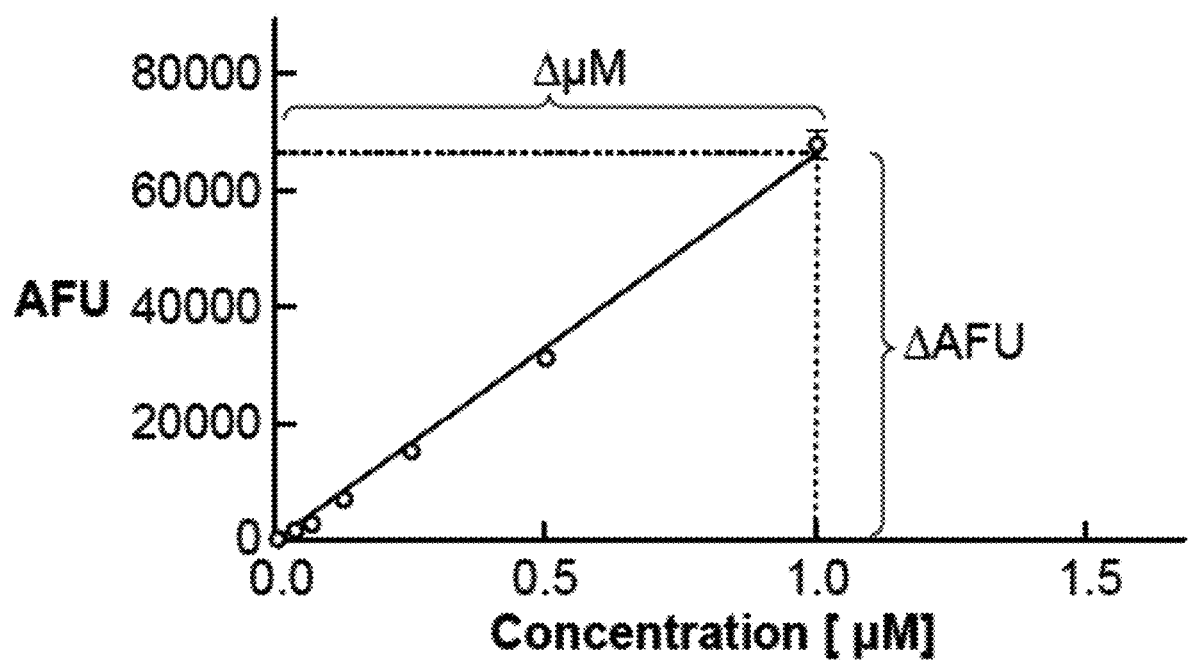
FIG. 2 is a standard curve for 2',7'-dichlorofluorescein (DCF), an oxidation product of the ROS detector compound 2',7'-dichlorodihydrofluorescein diacetate ($H_2$DCFDA). The standard curve was generated by graphing fluorescence (AFU) exhibited by dichlorofluorescein (DCF) as a function of DCF concentration (in $\mu M$), in accordance with an embodiment of the disclosure.

FIG. 2 is a standard curve for 2',7'-dichlorofluorescein (DCF) which was generated by graphing fluorescence (AFU) exhibited by DCF as a function of DCF concentration (in µM). In the DCF standard curve, ΔAFU=66681 corresponds to 1 µM of DCF. Extrapolation from the DCF standard curve provided the definition of one milliunit of FXN fusion protein as being the amount of FXN fusion protein necessary to catalyze the generation of 1 micromole (µM) of DCF per minute, based on the following formula:

$$V_f = \Delta AFU/min = \Delta \mu M/min.$$

Thus, the amount of an FXN protein necessary to achieve a maximum initial velocity $V_i=1$ is defined as a milliunit of FXN protein.

The present results demonstrate, for the first time, that an FXN protein, such as FXN fusion protein, functions as a redox sensitive enzyme, and is capable of catalyzing oxidation of hydroquinone with a concomitant production of superoxide. The redox activity of FXN fusion protein is enhanced in the presence of metal ions, such as $Mn^{2+}$ and $Fe^{3+}$. These experiments also enabled the present inventors to define activity of an enzymatic unit of FXN fusion protein.

Figure 3A:
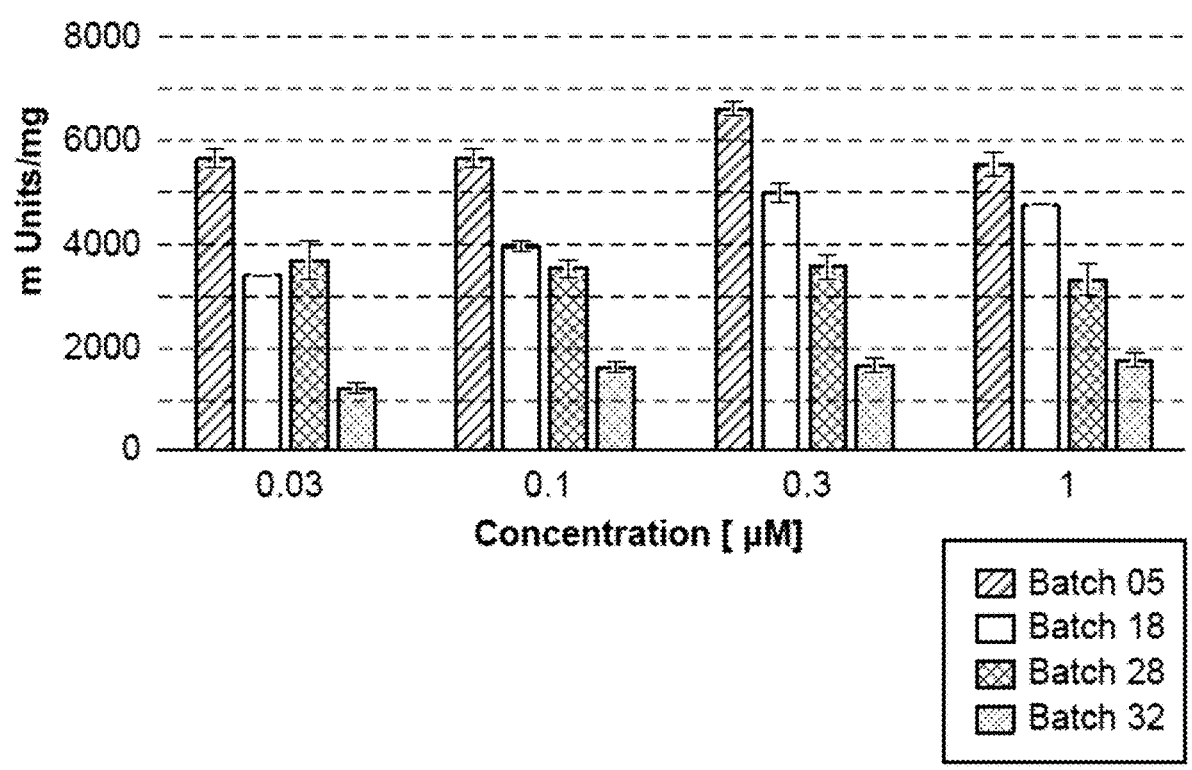
FIG. 3 shows the specific activity of various batches of an exemplary FXN fusion protein, where the different batches are at different concentrations of the FXN fusion protein and upon treatment with NADH or NADPH. Panel A of FIG. 3 is a bar graph showing the specific activity (expressed in milliunits per milligram, mUnits/mg) of four different batches of the FXN fusion protein (Batch 05, 18, 28 and 32) at various concentrations of the FXN fusion protein (0.03 $\mu M$, 0.1 $\mu M$, 0.3 $\mu M$, and 1 $\mu M$), in accordance with an embodiment of the disclosure. Panel B of FIG. 3 is a bar graph showing the specific activity (mUnits/mg) of the FXN fusion protein in the presence of $Fe^{3+}$, $Fe^{3+}$ and NADH, and $Fe^{3+}$ and NADPH, in accordance with an embodiment of the disclosure.
Figure 3B:
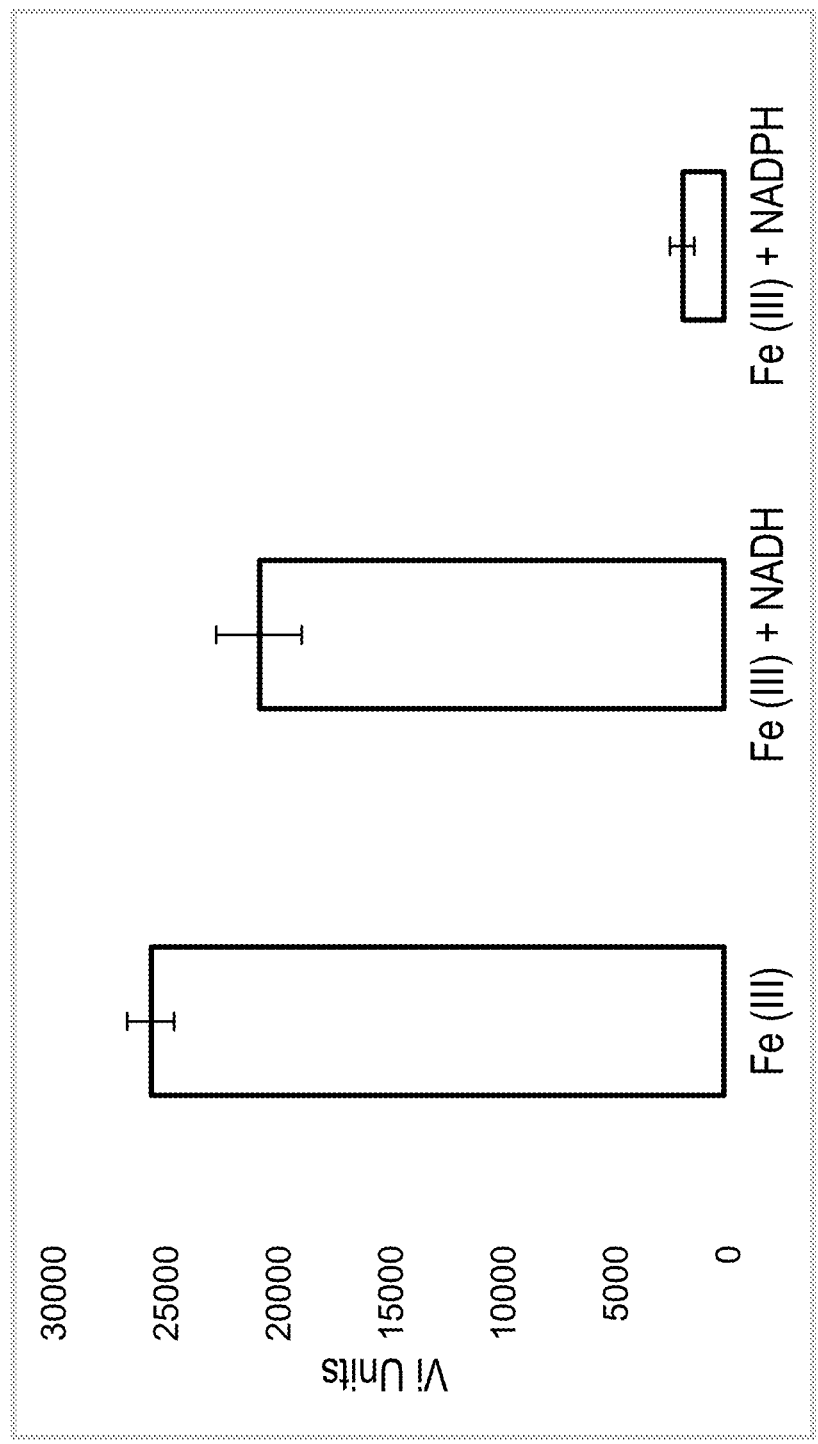

Example 3. Comparison of Activity in Different Batches of FXN Fusion Protein and in the Presence of NADH or NADP Once activity of an enzymatic unit of the exemplary FXN fusion protein was defined, the HQ assay was used to compare the specific activity (defined as mUnits per mg of the FXN fusion protein) of four different batches of the FXN fusion protein of SEQ ID NO: 12. The results of the experiment are presented in Panel A of FIG. 3. Specifically, Panel A of FIG. 3 is a bar graph showing the specific activity (expressed in milliunits per milligram, mUnits/mg) of four different batches of FXN fusion protein (Batch 05, 18, 28 and 32) at various concentrations of the FXN fusion protein (0.03 μM, 0.1 μM, 0.3 μM, and 1 μM). The results presented in Panel A of FIG. 3 indicate that the specific activity of each tested batch of FXN fusion protein was relatively constant across the four different concentrations of FXN fusion protein. Furthermore, batch 32 is the least active, with an average activity of 1582 mUnits/mg, while batch 05 is the most active, with an average activity of 5790 mUnits/mg.

Redox activity of the FXN fusion protein was also measured in the presence of NADPH and NADH. Panel B of FIG. 3 is a bar graph showing the specific activity (mUnits/mg) of the FXN fusion protein in the presence of $Fe^{3+}$, $Fe^{3+}$ and NADH, and $Fe^{3+}$ and NADPH. The results presented in Panel B of FIG. 3 indicate that addition of NADPH to the assay significantly diminished ROS production, inhibiting the redox activity of the FXN fusion protein, while addition of NADH did not affect the redox activity of the FXN fusion protein.

Example 4: Activity of FXN Fusion Protein is Susceptible to Elevated Temperature Storage Conditions The goal of this experiment was to evaluate thermal stability of an exemplary FXN fusion protein by evaluating the activity of the FXN fusion protein after short-term storage (one month) at different temperatures. FXN fusion protein of SEQ ID NO: 12 was used in this experiment. The storage conditions tested in the study and the corresponding results are summarized in Table below.

TABLE 10

Figure 4A:
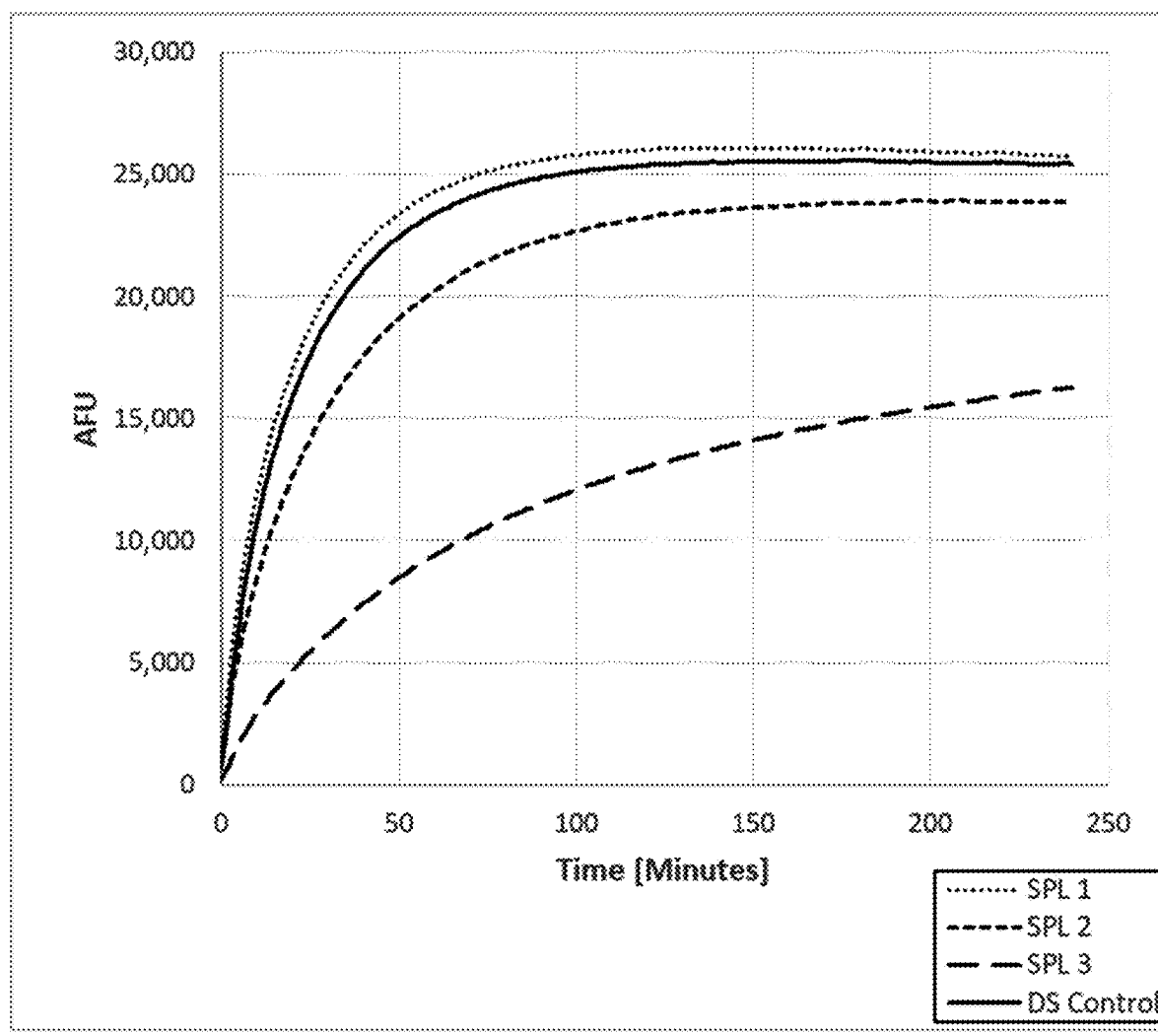
FIG. 4 shows the effect of storage temperature on the HQ-dependent superoxide generation activity of an exemplary FXN fusion protein. Panel A of FIG. 4 is a graph showing the kinetics of superoxide generation in the presence of the FXN fusion protein that has been stored at −60° C., 2-4° C. and 25° C., as compared to the drug substance (DS) control, in accordance with an embodiment of the disclosure. Panel B of FIG. 4 is a bar graph showing the maximum initial velocity (Vi) of superoxide generation in the presence of the FXN fusion protein that has been stored at −60° C., 2-4° C. and 25° C., as compared to the drug substance (DS) control, in accordance with an embodiment of the disclosure.
Figure 4B:
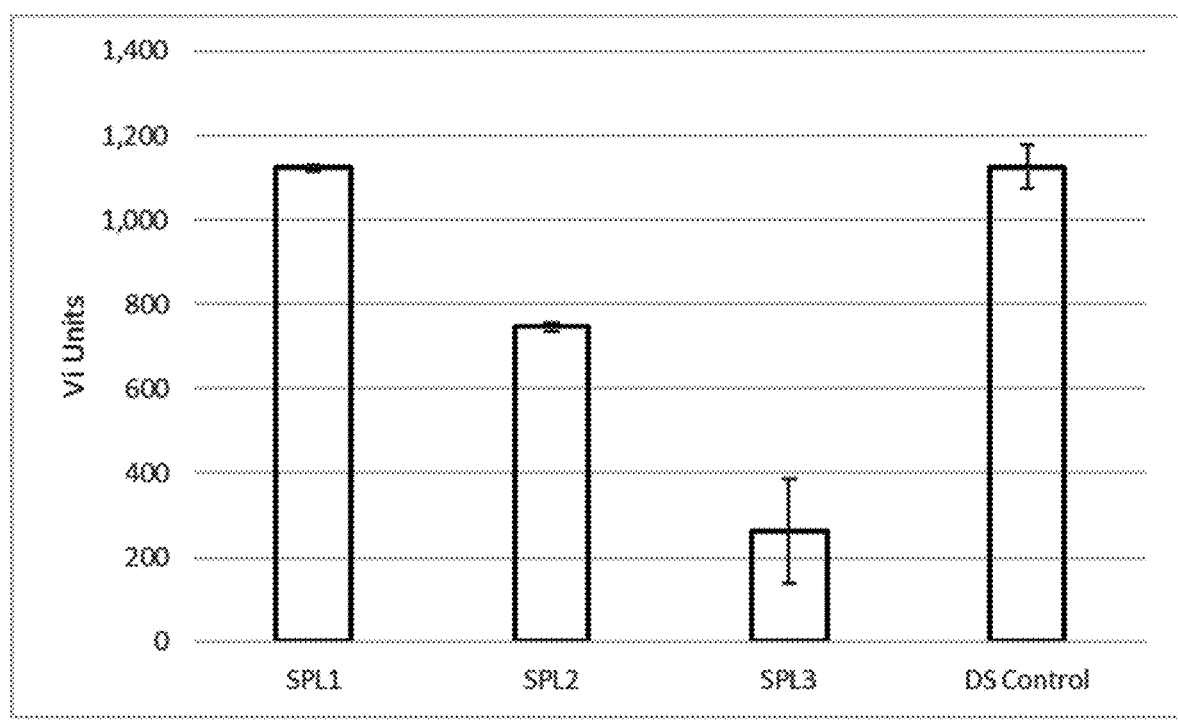

Conditions for temperature stability study of an exemplary FXN fusion protein (FIG. 4, Panel A)

| Sample Name | Description | Result (% activity) |
|---|---|---|
| SPL1 | 1 mL of FXN fusion protein at −60° C. for 1 month | 100% (1123 $V_i$ units) |
| SPL2 | 1 mL of FXN fusion protein at 2-4° C. for 1 month | 66.4% (746 $V_i$ units) |
| SPL3 | 1 mL of FXN fusion protein at 25° C. for 1 month | 23.4% (263 $V_i$ units) |
| Drug substance (DS) control | Drug substance (DS) control (stored at −80° C.) | 100.2% (1126 $V_i$ units) |

The results of the experiment are also presented in FIG. 4. Specifically, Panel A of FIG. 4 is a graph showing the kinetics of superoxide generation in the presence of an exemplary FXN fusion protein that has been stored at −60° C. (SPL1), 2-4° C. (SPL2) and 25° C. (SPL3), as compared to the DS control. Panel B of FIG. 4 is a bar graph showing the maximum initial velocity ($V_i$) of superoxide generation in the presence of an exemplary FXN fusion protein that has been stored at −60° C. (SPL1), 2-4° C. (SPL2) and 25° C. (SPL3), as compared to the DS control.

The results presented in FIG. 4 and in Table 10 demonstrate that storage of the exemplary FXN fusion protein in conditions other than −60° C. for one month resulted in decreased activity of the exemplary FXN fusion protein in the HQ Assay. This also demonstrate that incubation of the exemplary FXN fusion protein at temperatures higher than −60° C. decreases its activity in the HQ assay.

Figure 5:
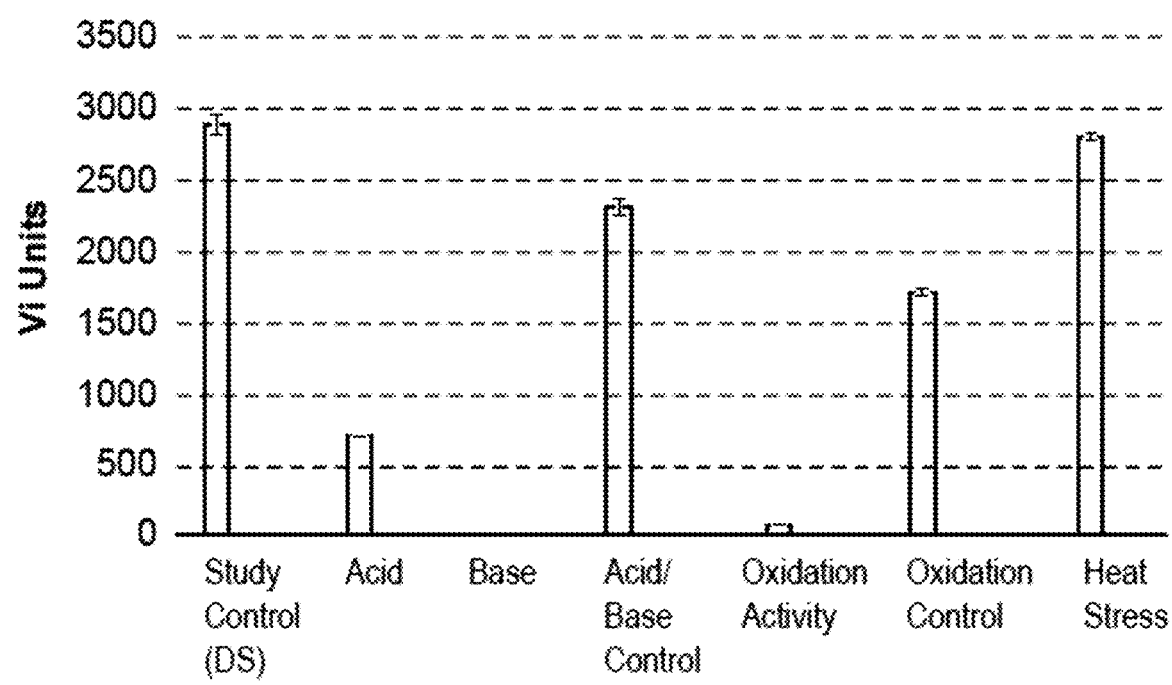
FIG. 5 shows the effect of chemical treatments on the activity of an exemplary FXN fusion protein. Specifically.

Example 5. Activity of an Exemplary FXN Fusion Protein is Susceptible to Chemical Stress The goal of this experiment was to evaluate stability to chemical stress of an exemplary FXN fusion protein by evaluating the activity of the exemplary FXN fusion protein after its exposure to chemical stressors that may trigger protein denaturation and/or degradation of the FXN fusion protein. FXN fusion protein of SEQ ID NO: 12 was used in this experiment. The storage conditions tested in the study and the corresponding results are shown in FIG. 5 and also summarized in Table 11 below.

TABLE 11

Conditions for chemical stability study of an exemplary FXN fusion protein

| Sample Name | Description | Result (% activity) |
|---|---|---|
| Study control | 1 mL of FXN fusion protein at 2-8° C. for 2 hours | 100% (2,908 $V_i$ units) |
| Acid stress | 1 mL of FXN fusion protein, pH ≤4, at 37° C. for 2 days | 23.7% (689 $V_i$ units) |
| Alkaline stress | 1 mL of FXN fusion protein, pH ≥10, at 37° C. for 2 days | 0.02% (0.7 $V_i$ units) |
| Acid and alkaline control | 1 mL of FXN fusion protein at 37° C. for 2 days | 79.7% (1,730 $V_i$ units) |
| Oxidation | 1 mL of FXN fusion protein 0.05% peroxide at 37° C. for 2 hours | 2.2% (63 $V_i$ units) |

TABLE 11-continued

Conditions for chemical stability study of an exemplary FXN fusion protein

| Sample Name | Description | Result (% activity) |
| --- | --- | --- |
| Oxidation control | 1 mL of FXN fusion protein at 37° C. for 2 hours | 59.5% (1,730 $V_i$ units) |
| Heat stress | 1 mL of FXN fusion protein at 50° C. for 2 hours | 96.9% (2,820 $V_i$ units) |

Briefly, study control was stored at 2-8° C. over the course of the study. Each treatment was conducted as follows:

i. Acid treatment: 1N HCl was added to the solution containing FXN fusion protein until a pH≤4 was reached. The sample was kept at 37° C. for 2 days, and then the buffer exchanged for the buffer of the DS formulation. The sample was stored at 2-8° for the remainder of the study.

ii. Alkaline treatment: 1M Tris base was added to the solution containing FXN fusion protein until a pH≥10 was reached. The sample was kept at 37° C. for 2 days, and then the buffer was exchanged for the buffer of the DS formulation. The sample was stored at 2-8° C.

iii. Acid and Base control: solution containing FXN fusion protein was stored at 37° C. for 2 days, and then stored at 2-8° C.

iv. Oxidation stress treatment: exemplary FXN fusion protein was incubated in the presence of 0.05% hydrogen peroxide at 37° C. for 2 hours and then stored at 2-8° C.

v. Oxidation control: exemplary FXN fusion protein was incubated at 37° C. for 2 hours and then stored at 2-8° C.

vi. Heat stress treatment: exemplary FXN fusion protein was incubated at 50° for 2 hours then stored at 2-8° C.

All samples were analyzed for appearance, pH, protein quantification (by A280), size-exclusion ultra-performance liquid chromatography (SE-UPLC), reversed-phase high-performance liquid chromatography (RP-HPLC), ion-exchange high-performance liquid chromatography (IE-HPLC), reduced capillary electrophoresis sodium dodecyl sulfate (rCE-SDS), non-reduced capillary electrophoresis sodium dodecyl sulfate (nrCE-SDS), and free thiol (data not shown). The concentration of FXN fusion protein was determined by Western blot, and redox activity was determined using the HQ assay as described above.

The results of the HQ activity are presented in FIG. 5. Specifically, FIG. 5 is a bar graph showing the maximum initial velocity ($V_i$) of superoxide generation of all tested samples. The results indicate that the FXN fusion protein, to a large extent, was resistant to heat stress when applied for 2 hours. The results also indicate that the FXN fusion protein was susceptible to alkaline and oxidation stress, and partly susceptible to acid stress.

Example 6. Activity of an Exemplary FXN Fusion Protein in the Presence of Different Metal Ions The goal of this experiment was to evaluate the HQ-dependent superoxide generating activity of an exemplary FXN fusion protein in the presence of different metal ions. FXN fusion protein of SEQ ID NO: 12 was used in this experiment. Kinetics of superoxide generation was evaluated in reaction mixtures containing 20 µM HQ, 5 µM Metals, 5 µM FXN fusion protein, 0.25 µM H$_2$DCF in 50 mM Tris-HCL buffer at pH 8.0. The metal ions tested in the experiment included $Mn^{2+}$, $Fe^{3+}$, $Zn^{2+}$, $Cu^{2+}$ and $Mg^{2+}$.

Figure 6:
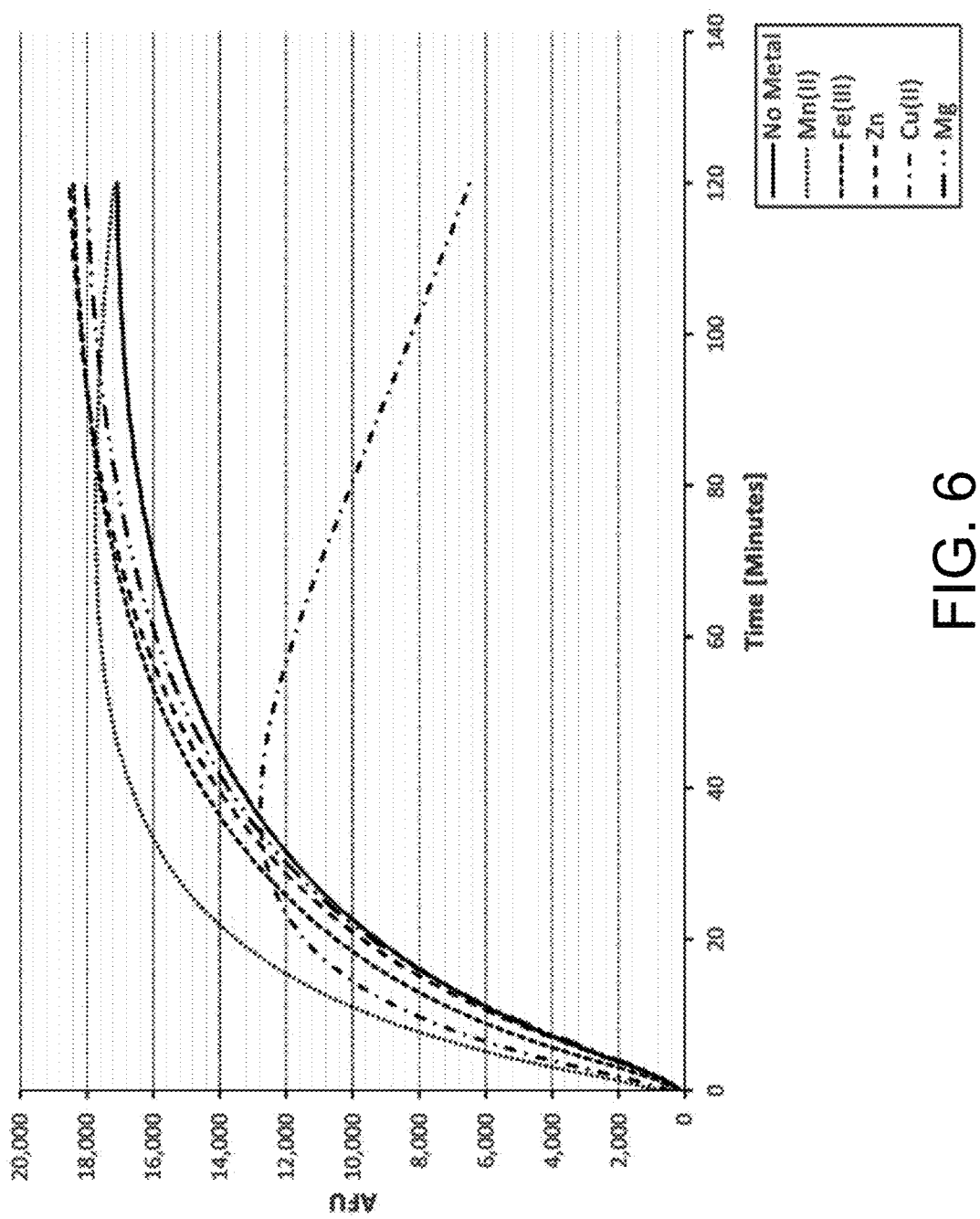
FIG. 6 is a graph showing the kinetics of HQ-dependent superoxide generation activity of an exemplary FXN fusion protein in the presence of different metal ions.

FIG. 6 is a graph showing the kinetics of HQ-dependent superoxide generation activity of the exemplary FXN fusion protein in the presence of different metal ions. The data presented in FIG. 6 demonstrates that the FXN fusion protein exhibited the highest activity in the presence of $Mn^{2+}$.

Example 7. pH Dependence of the Activity of an Exemplary FXN Fusion Protein

The goal of this experiment was to evaluate pH dependence of HQ-dependent superoxide generating activity of an exemplary FXN fusion protein. FXN fusion protein of SEQ ID NO: 12 was used in this experiment. Specifically, kinetics of superoxide generation by an exemplary FXN fusion protein was evaluated at pHs ranging from 7.0 to 9.0. Each reaction mixture contained 5 µM HQ, 5 µM Fe(III) sulfate, 0.05 µM H$_2$DCF and 10 µM exemplary FXN fusion protein in 50 mM Tris-HCL at pH of 7.0, 7.4, 7.8, 8.0, 8.2, 8.5 and 9.0.

The assay plate was placed in the plate reader and the kinetic read began immediately after all assay ingredients were mixed together. The plate reader settings were as follows: 2-hour kinetic scan with a Fluorescent read (excitation 485/20, emission 528/25, and a gain of 50) every 5-minutes with a 10 second shake between reads. Maximum initial velocity (Vi) was determined for each well by measuring fastest change in arbitrary fluorescence unit (AFU) over 5 data points.

Figure 7:
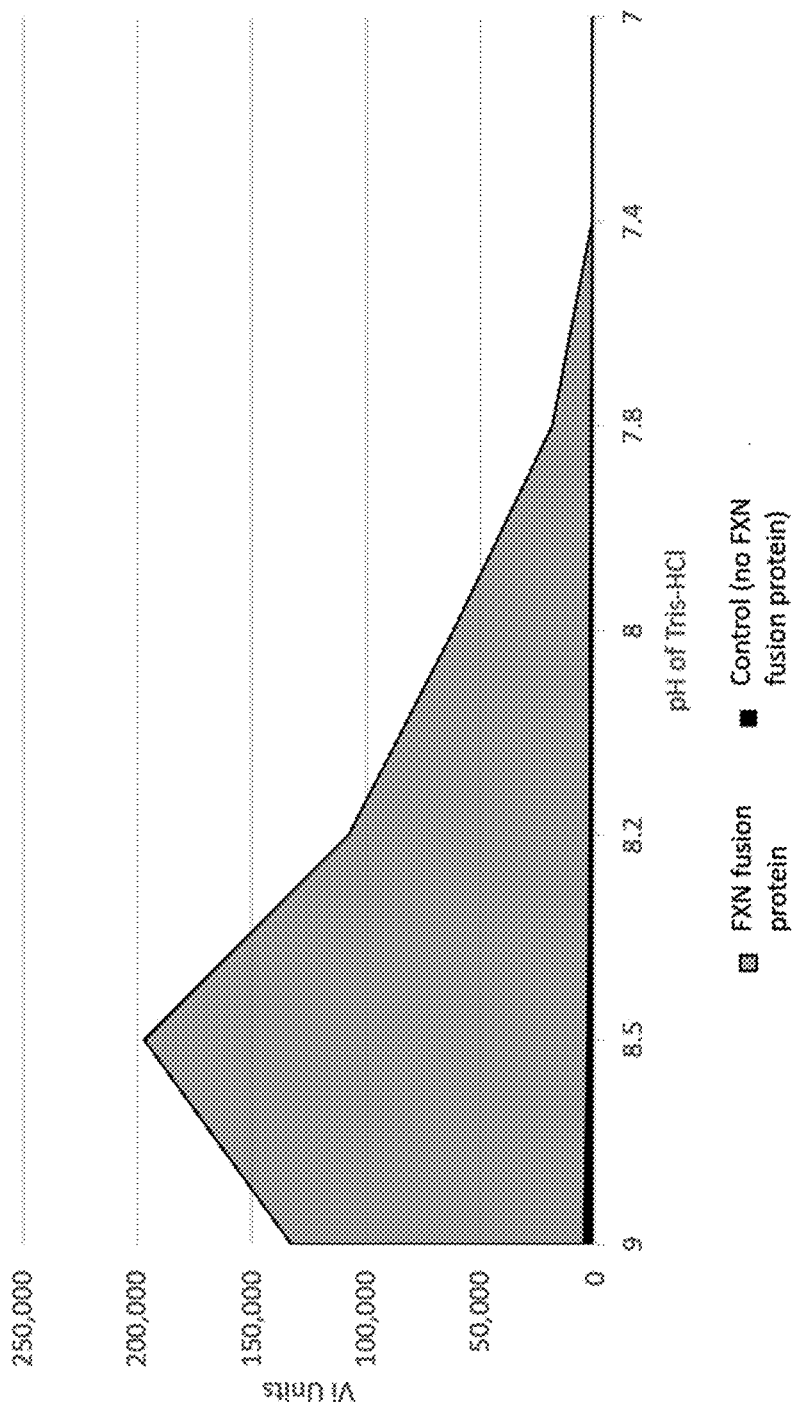
FIG. 7 is a graph showing Vi as a measurement of activity of an exemplary FXN fusion protein as a function of pH.

FIG. 7 is a graph showing $V_i$ as a measurement of activity of an exemplary FXN fusion protein as a function of pH. The data presented in FIG. 7 demonstrates that the superoxide-generating activity of the exemplary FXN fusion protein is pH dependent. Specifically, the FXN fusion protein displays almost no activity at pH of 7.4 or lower. As the pH increases to greater than 7.4, the activity of the exemplary FXN fusion protein increases, and peaks at pH of about 8.5. This optimal pH range for the exemplary FXN fusion protein overlaps with the pH of the mitochondrial matrix of about 7.8, which is higher than the pH of the cytosol of about 7.4.

Example 8. A High Throughput Screen (HTS) to Identify Compounds that can Affect FXN Activity The goal of this experiment was to identify compounds capable of modulating activity of an FXN protein by using use HQ assay of the present disclosure and a High Throughput Screen (HTS). FXN fusion protein of SEQ ID NO: 12 was used in this experiment. The experiment consisted of two parts. In the first part of the experiment, performance of the HQ assay at the conditions used for the HTS was validated. In the second part of the assay, a series of screens of a 770 compound library were conducted to identify compounds capable of enhancing activity of an exemplary FXN fusion protein.

Evaluation of Assay Performance

The goal of the first part of the experiment was to validate performance of the HQ assay at the conditions used for the HTS. To this end, the HQ assay was characterized by measuring statistical parameters, such as signal-to-background (S/B) ratio, Z' factor (which is a measure of the statistical robustness of the assay readout), and intra- and inter-plate variability. To this end, two 96-well plates were each split into 9 sections: 4 sections in each plate contained an exemplary FXN fusion protein at the concentration of 10 µM (high control); 4 sections contained the exemplary FXN fusion protein at the concentration of 0.5 µM (low control);

and 1 section contained only the assay mix without the FXN fusion protein (blank control).

$H_2DCF$ was activated by incubating in the dark 1 mL of 1 mM $H_2DCF$-DA in 20 mL of 0.01 M NaOH for 30 minutes while stirring. Subsequently, 75 mL of 33 mM $NaH_2PO_4$ was added to the activation mixture to yield a final $H_2DCF$ concentration of 10 μM. This solution was stored at 4° C. and protected from light until use. The assay mix in each well contained 50 mM Tris-HCL (pH 8.0), 50 μM HQ, 1 μM $MnCl_2$, 0.5 μM activated $H_2DCF$ and the exemplary FXN fusion protein at the concentration of 10 μM (high control), 0.5 μM (low control) and 0 μM (blank control). After the assay mix was added to the plate, the plate was immediately placed in the plate reader, and the kinetic read was initiated. The plate reader settings were as follows: 45-minute kinetic scan with a Fluorescent read (excitation 482/20, emission 530/25, and a gain of 50) every minute with a 3 second shake in between reads. Maximum initial velocity (Vi) was determined for each well by measuring the fastest change in arbitrary fluorescence unit (AFU) over 5 data points. The statistical parameters, such as signal-to-background (S/B) ratio, Z' factor, and intra- and inter-plate variability were calculated to characterize the assay performance.

Figure 8:
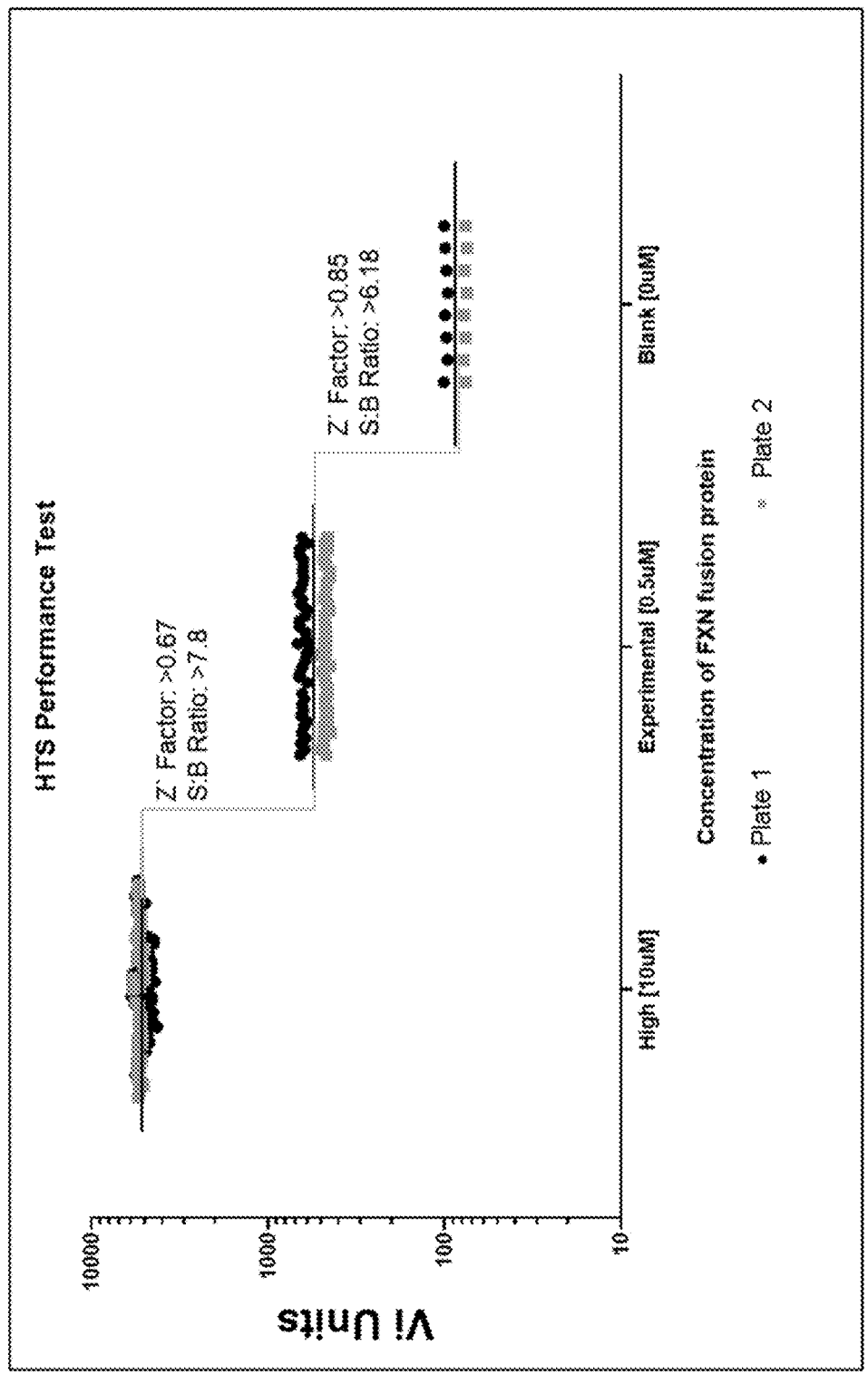
FIG. 8 is a graph showing the results of the experiment designed to validate performance of the FXN activity assay of the present disclosure at the conditions used for the High Throughput Screening (HTS). Specifically, the graph in FIG. 8 shows Vi values determined for each tested sample containing 10 $\mu M$ FXN fusion protein (high control), 5 $\mu M$ FXN fusion protein (low control) and 0 $\mu M$ FXN fusion protein (blank control) for plates 1 and 2.

The results are presented in FIG. 8 and in Table 12 below. FIG. 8 is a graph showing Vi values determined for each tested sample containing 10 μM FXN fusion protein (high FXN control), 5 μM FXN fusion protein (low FXN control) and 0 μM FXN fusion protein (blank control) for plates 1 and 2. Based on this data, the Z factor for the high FXN control samples was calculated to be greater than 0.67 and the associated S/B ratio was calculated to be greater than 7.8, while the Z factor for the low FXN control samples was calculated to be greater than 0.85 and the S/B ratio was calculated to be greater than 6.18. Table 12 below presents data used to evaluate plate-to-plate variability of the HQ assay.

TABLE 12

Vi values for each tested condition and the associated statistical parameters

| | Sample | Mean Vi | % CV | N (number of wells) |
|---|---|---|---|---|
| Plate 1 | High control (10 gM FXN fusion protein) | 5390.0 | 3.8 | 48 |
| | Low control (0.5 μM FXN fusion protein) | 471.0 | 2.8 | 40 |
| | Blank control (0 μM FXN fusion protein) | 76.4 | 1.7 | 8 |
| Plate 2 | High control (10 μM FXN fusion protein) | 4995.1 | 9.1 | 48 |
| | Low control (0.5 μM FXN fusion protein) | 635.5 | 3.8 | 40 |
| | Blank control (0 μM FXN fusion protein) | 98.6 | 1.9 | 8 |
| Plates 1 and 2 combined | High control (10 μM FXN fusion protein) | 5192.5 | 7.7 | 96 |
| | Low control (0.5 μM FXN fusion protein) | 553.2 | 15.4 | 80 |
| | Blank control (0 μM FXN fusion protein) | 87.5 | 13.2 | 16 |

The results shown in FIG. 8 and Table 12 demonstrate that the performance of the HQ assay is suitable for an HTS experiment at the tested conditions.

High Throughput Screen (HTS)

The goal of the part of the experiment was to conduct a high throughput screen of a drug library using the HQ assay of the present disclosure to identify compounds that modulate the activity of FXN protein in this assay. The HTS was conducted using the SCREEN-WELL® FDA approved drug library V2 purchased from Enzo Life Sciences (Product #BML-2843-0100). This library contains over 770 compounds that are FDA approved and have known and well-characterized bioactivity, safety and bioavailability. The library also avoids irrelevant compounds, such as herbicides, insecticides, sunscreen agents, and cytotoxic agents. The compounds in the SCREEN-WELL® FDA approved drug library V2 were screened for their ability to enhance activity of an exemplary FXN fusion protein.

Figure 9:
FIG. 9 is a flowchart showing the three steps involved in the HTS experiment and the associated results.

The summary of the HTS experiment that was conducted is illustrated in FIG. 9. Specifically, FIG. 9 is a flowchart showing the three steps involved in the HTS experiment and the associated results. The first step included the primary screen in which the compounds in the SCREEN-WELL® FDA approved drug library V2 were screened for FXN enhancing activity. In this screen, 17 hits were identified that demonstrated greater than 30% FXN activity enhancement. The second step included a confirmatory screen, in which the 17 compounds identified in the primary screen were re-screened, and 16 compounds were confirmed as enhancing FXN activity by greater than 2× the standard deviation of the low FXN control wells included on each assay plate. The third step included a counter screen, in which the 16 compounds identified in the confirmatory screen were screened in the absence of the exemplary FXN fusion protein. In this screen, 2 out of the 16 compounds were identified whose FXN enhancing activity was strictly dependent on the presence of FXN.

The primary screen was conducted using the following procedure. The complete assay mix was freshly prepared just prior to addition to the assay plate and included 50 mM Tris-HCL (pH 8.0), 50 μM HQ, 1 μM $MnCl_2$, 0.5 μM activated $H_2DCF$, the exemplary FXN fusion protein at the concentration of 0.5 μM and a test compound at the final concentration of 10 μM. In addition, each plate also included internal controls containing the exemplary FXN fusion protein at the concentration of 10 μM (upper limit control), 0.5 μM (lower limit control) or 0 μM (vehicle for blank control) in 1% DMSO and in water. The controls in both DMSO and water were included because the library compounds were dissolved in either DMSO or water. After all components of the assay were mixed together, the plates were immediately placed into the plate reader, and the kinetic read was initiated. The plate reader settings were as follows: 45-minute kinetic scan with a Fluorescent read (excitation 482/20, emission 530/25, and a gain of 50) every minute with a 3 second shake in between reads.

Maximum initial velocity (Vi) was determined for each well by measuring the fastest change in arbitrary fluorescence unit (AFU) over 5 data points anywhere on the curve. Average of Vi values for control wells containing 0.5 μM FXN fusion protein were calculated, and a window of 30% above plate average determined as the cutoff for hit compounds.

Figure 10:
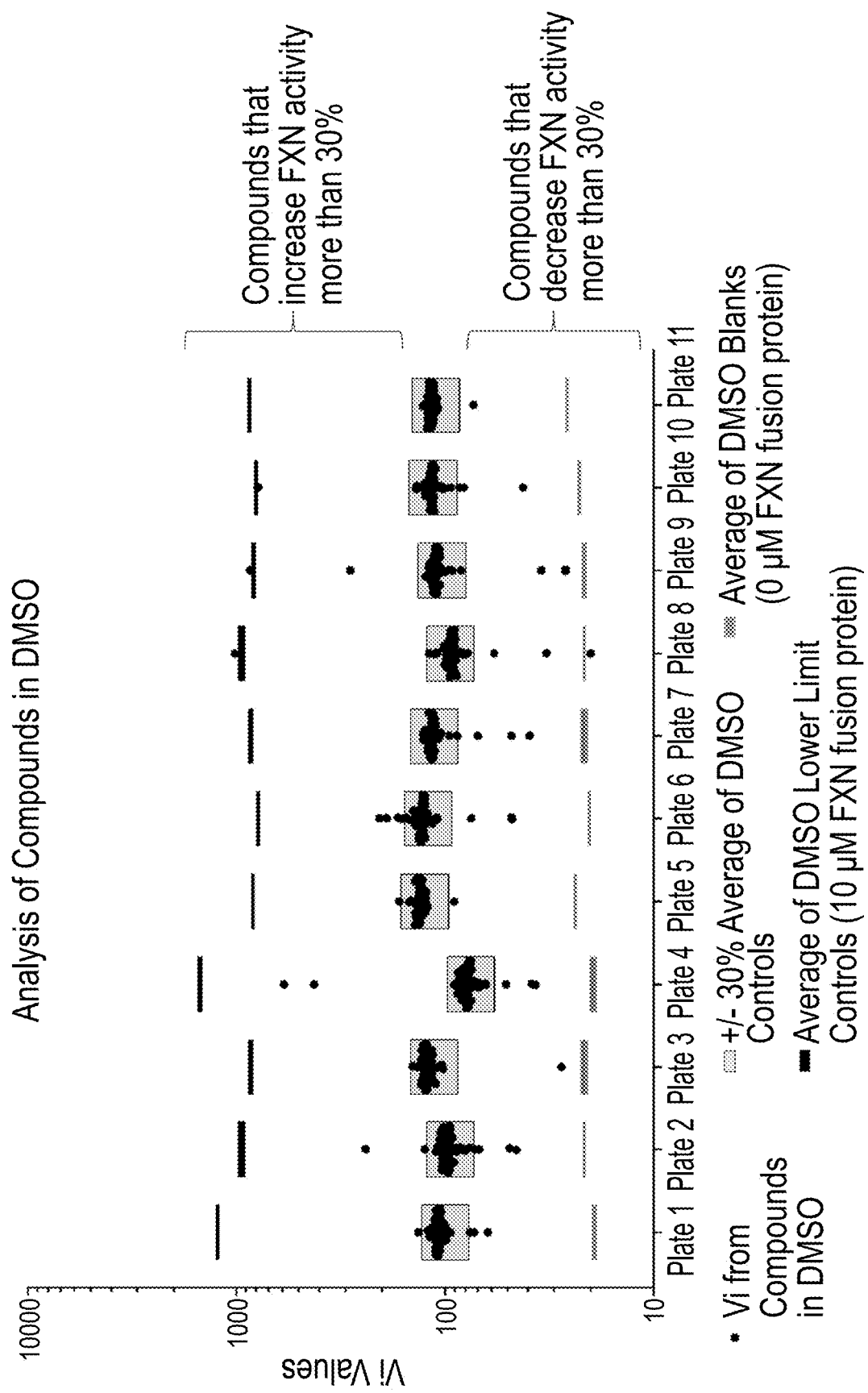
FIG. 10 is a box plot showing the results of the HTS primary screen of compounds in DMSO, including the compounds that increase FXN activity by more than 30%, compounds that decrease FXN activity by more than 30% and compounds that cause less than a 30% change in the FXN activity.

FIG. 10 is a box plot showing the results of the HTS primary screen of compounds in DMSO, including the compounds that increase FXN activity by more than 30%, compounds that decrease FXN activity by more than 30% and compounds that cause less than a 30% change in the FXN activity. Any compound with a Vi value higher than the cutoff was qualified for the secondary screen. As indicated above, in the primary screen, 17 hits were identified that demonstrated greater than 30% FXN activity enhancement.

The confirmatory screen was conducted using the procedure similar to the one used for the primary screen. In the confirmatory screen, 16 compounds were confirmed as enhancing FXN activity by more than 2× the standard deviation of the low FXN control wells included on each plate that contained 0.5 μM FXN fusion protein.

Figure 11:
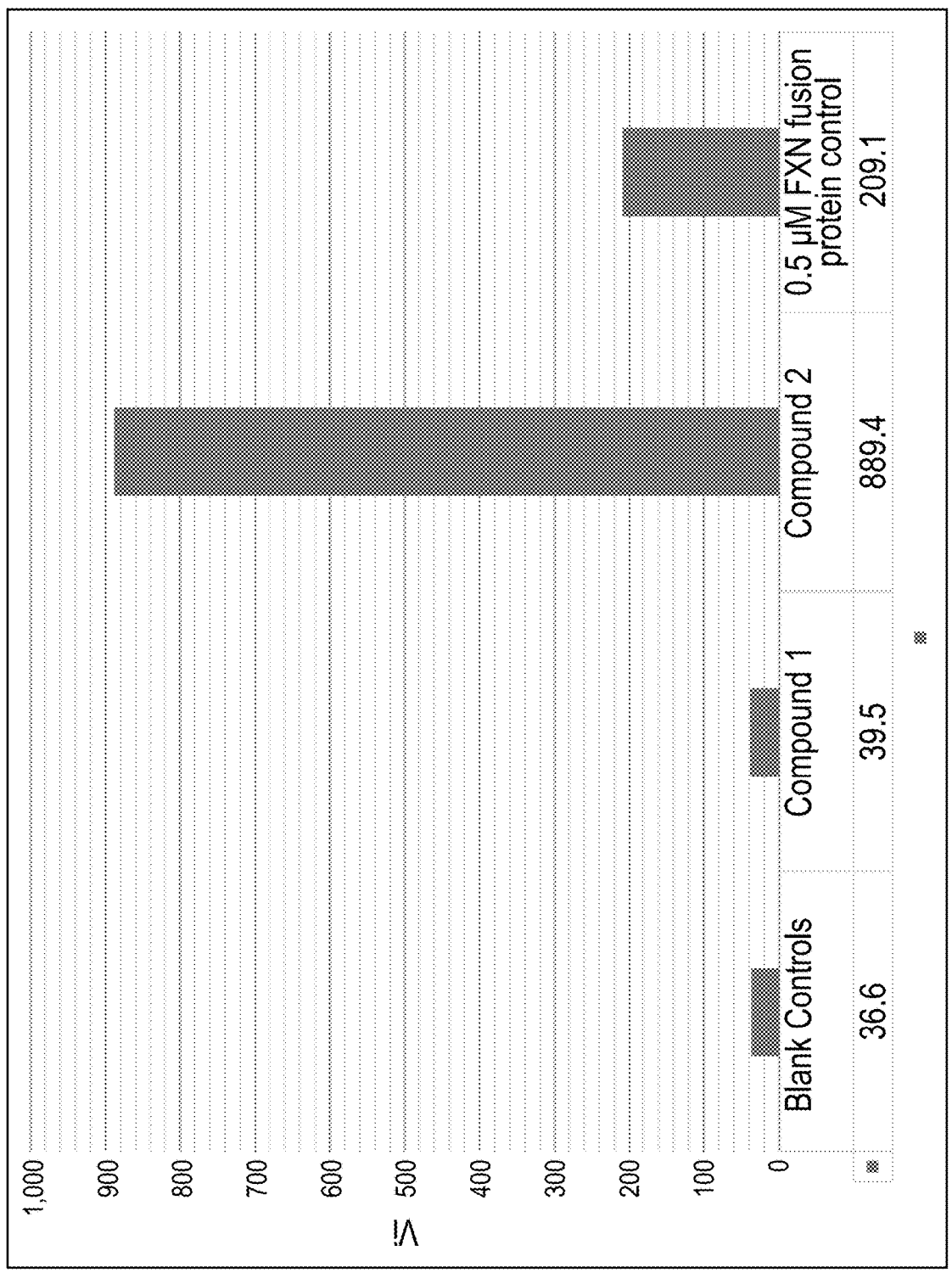
FIG. 11 is a bar graph showing exemplary results of a confirmatory screen for Compound 1 and Compound 2, with Compound 1 passing the counter screen as having no activity in the absence of the FXN fusion protein; and Compound 2 failing the counter screen as having activity in the absence of the FXN fusion protein.

The counter screen identified compounds with FXN enhancing activity that was dependent on the presence of the FXN fusion protein. In this screen, compounds with the FXN activity that does not deviate by more than 2× the standard deviation from the FXN activity displayed by the internal vehicle controls were selected. FIG. 11 is a bar graph showing exemplary results of the confirmatory screen for Compound 1 and Compound 2. The results shown in FIG. 11 indicate that Compound 1 passed the counter screen because it displayed no activity in the absence of the FXN fusion protein; while Compound 2 was disqualified because it displayed activity in the absence of the FXN fusion protein. In the counter screen, 2 out of 16 compounds from the confirmatory screen were identified as having FXN enhancing activity that was dependent on the presence of FXN.

What is claimed is:

1. A method for measuring enzymatic activity of a Frataxin (FXN) protein, wherein said enzymatic activity comprises enzymatically catalyzed generation of reactive oxygen species (ROS), said method comprising:
   (a) combining said FXN protein with a reducing agent and an ROS detector compound, thereby producing an assay mixture;
   (b) measuring the amount of ROS generated in the assay mixture over time; and
   (c) determining an enzymatic parameter associated with the ROS generating activity of the FXN protein;
wherein said FXN protein facilitates oxidation of the reducing agent and generation of ROS, such that the amount of ROS generated is higher than the amount of ROS generated in the assay mixture comprising the reducing agent and the ROS detector compound without the FXN protein.

2. The method of claim 1, comprising combining said FXN protein with a reducing agent and an ROS detector compound at a pH of about 7.4 to about 9.

3. The method of claim 2, further comprising adding a metal ion into the assay mixture.

4. The method of claim 1, comprising combining said FXN protein with a reducing agent and an ROS detector compound in the absence of metal ions.

5. The method of claim 4, further comprising adjusting pH of the assay mixture to pH of about 7.4 to about 9.

6. The method of claim 1, comprising combining said FXN protein with a reducing agent and an ROS detector compound in the absence of iron ions.

7. The method of claim 6, further comprising adjusting pH of the assay mixture to pH of about 7.4 to about 9.

8. The method of claim 1, further comprising adding a metal ion into the assay mixture.

9. The method of claim 8, wherein the metal ion is selected from the group consisting of $Mn^{2+}$, $Fe^{3+}$, $Zn^{2+}$, $Cu^{2+}$ and $Mg^{2+}$.

10. The method of claim 1, wherein the amount of ROS generated is measured at regular time intervals.

11. The method of claim 1, wherein step (c) comprises determining maximum initial velocity (Vi) of ROS generation in the assay mixture.

12. The method of claim 1, wherein step (c) comprises determining time to maximum initial velocity (Ti).

13. The method of claim 1, wherein step (c) comprises determining the unit activity of the FXN protein at pH of about 7.4 to about 9.

14. The method of claim 1, wherein the reducing agent is an organic compound.

15. The method of claim 14, wherein the reducing agent is a reduced quinone compound.

16. The method of claim 15, wherein the reduced quinone compound is hydroquinone.

17. The method of claim 1, wherein the ROS detector compound is a superoxide anion detection reagent or a hydrogen peroxide detection reagent.

18. The method of claim 17, wherein the ROS detector compound is 2',7'-dichlorodihydrofluorescein ($H_2DCF$) diacetate.

19. The method of claim 1, wherein the reducing agent and the ROS detector compound are different compounds.

20. The method of claim 19, wherein the reducing agent is dihydroquinone and the ROS detector compound is 2',7'-dichlorodihydrofluorescein ($H_2DCF$).

21. The method of claim 1, wherein the FXN protein is comprises full-length hFXN (SEQ ID NO: 1) or mature hFXN (SEQ ID NO: 2).

22. The method of claim 1, wherein the FXN protein is an FXN fusion protein comprising full-length hFXN and a cell penetrating peptide (CPP).

23. The method of claim 22, wherein the CPP comprises HIV-TAT or a variant or derivative thereof.

24. The method of claim 22, wherein the FXN fusion protein comprises SEQ ID NO: 12.

25. A method for performing quality control on a sample comprising a FXN protein, said method comprising measuring activity of an FXN protein in accordance with the method of claim 1.

* * * * *

UNITED STATES PATENT AND TRADEMARK OFFICE
CERTIFICATE OF CORRECTION

PATENT NO.       : 11,988,675 B2
APPLICATION NO.  : 17/105149
DATED            : May 21, 2024
INVENTOR(S)      : Joan David Bettoun It is certified that error appears in the above-identified patent and that said Letters Patent is hereby corrected as shown below:

In the Claims

At Column 54, Claim 21, Lines 6-7: replace "wherein the FXN protein is comprises" with -- wherein the FXN protein comprises --.

Signed and Sealed this
Twenty-fifth Day of June, 2024

Katherine Kelly Vidal
*Director of the United States Patent and Trademark Office*